United States Patent
Armstrong

(10) Patent No.: US 10,869,868 B2
(45) Date of Patent: Dec. 22, 2020

(54) TARGETING CHROMATIN REGULATORS INHIBITS LEUKEMOGENIC GENE EXPRESSION IN NPM1 MUTANT LEUKEMIA

(71) Applicant: Memorial Sloan Kettering Cancer Center, New York, NY (US)

(72) Inventor: Scott A. Armstrong, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/072,876

(22) PCT Filed: Jan. 26, 2017

(86) PCT No.: PCT/US2017/015168
§ 371 (c)(1),
(2) Date: Jul. 25, 2018

(87) PCT Pub. No.: WO2017/132398
PCT Pub. Date: Aug. 3, 2017

(65) Prior Publication Data
US 2019/0307750 A1    Oct. 10, 2019

Related U.S. Application Data

(60) Provisional application No. 62/287,419, filed on Jan. 26, 2016, provisional application No. 62/370,670, filed on Aug. 3, 2016.

(51) Int. Cl.
| *A61K 31/519* | (2006.01) |
| *A61P 35/02* | (2006.01) |
| *A61K 31/7064* | (2006.01) |
| *A61K 45/06* | (2006.01) |

(52) U.S. Cl.
CPC ........ *A61K 31/519* (2013.01); *A61K 31/7064* (2013.01); *A61K 45/06* (2013.01); *A61P 35/02* (2018.01)

(58) Field of Classification Search
CPC .. A61K 31/519; A61K 31/7064; A61K 45/06; A61P 35/02; C07D 495/04; C07D 519/00; C07D 495/16
See application file for complete search history.

(56) References Cited

U.S. PATENT DOCUMENTS

| 8,722,877 | B2 | 5/2014 | Chesworth et al. | |
| 9,216,993 | B2 * | 12/2015 | Grembecka | C07D 495/04 |
| 9,505,781 | B2 * | 11/2016 | Grembecka | C07D 495/04 |
| 9,505,782 | B2 * | 11/2016 | Grembecka | C07D 495/04 |
| 10,407,732 | B2 * | 9/2019 | Armstrong | A61P 43/00 |
| 10,526,341 | B2 * | 1/2020 | Tabar | A61K 31/519 |
| 2012/0142625 | A1 | 6/2012 | Olhava et al. | |
| 2014/0100184 | A1 | 4/2014 | Song et al. | |
| 2014/0275070 | A1 | 9/2014 | Grembecka et al. | |
| 2015/0342979 | A1 | 12/2015 | Pollock et al. | |

FOREIGN PATENT DOCUMENTS

| WO | WO 2008/070303 | 4/2009 |
| WO | WO 2011/029054 | 3/2011 |
| WO | WO 2012/075381 | 6/2012 |
| WO | WO 2012/075492 | 7/2012 |
| WO | WO 2012/075500 | 9/2012 |
| WO | WO 2012/082436 | 9/2012 |
| WO | WO 2014/026198 | 2/2014 |
| WO | WO 2014/039839 | 3/2014 |
| WO | WO 2014/100662 | 6/2014 |
| WO | WO 2015/017863 | 2/2015 |
| WO | WO 2015/169906 A1 | 11/2015 |
| WO | WO 2016/025649 | 2/2016 |

OTHER PUBLICATIONS

Verhaak et al., "Mutations in nucleophosmin (NPM1) in acute myeloid leukemia (AML): association with other gene abnormalities and previously established gene expression signatures and their favorable prognostic significance", 2005, Blood, 106(12), pp. 3747-3754. (Year: 2005).*
Schlenk et al., "Mutations and Treatment Outcome in Cytogenetically Normal Acute Myeloid Leukemia", 2008, The New England Journal of Medicine, 358(18), 1909-1918. (Year: 2008).*
Rau et al., "Nucleophosmin (NPM1) mutations in adult and childhood acute myeloid leukaemia: towards definition of a new leukaemia entity", 2009, Hematological Oncology, 27(4), pp. 171-181. (Year: 2009).*
Grembecka et al., "Menin-MLL inhibitors reverse oncogenic activity of MLL fusion proteins in leukemia", 2012, Nature Chemical Biology, 8(3), pp. 277-284. (Year: 2012).*
Kao et al., "High frequency of additional gene mutations in acute myeloid leukemia with MLL partial tandem duplication: DNMT3A mutation is associated with poor prognosis", 2015, Oncotarget, 6(32), pp. 33217-33225. (Year: 2015).*
Kuhn et al., "Targeting Chromatin Regulators Inhibits Leukemogenic Gene Expression in NPM1 Mutant Leukemia", 2016, Cancer Discovery, 6(10), pp. 116-1181. (Year: 2016).*

(Continued)

Primary Examiner — My-Chau T. Tran
(74) Attorney, Agent, or Firm — Foley & Lardner LLP

(57) ABSTRACT

Disclosed are methods for inhibiting proliferation of or inducing apoptosis in certain leukemia cells or both. The methods comprise contacting a leukemia cell exhibiting an NPM1 mutation with a pharmacologic inhibitor of interaction between MLL and menin. More broadly, disclosed are methods for treating a susceptible leukemia using pharmacologic inhibition of Menin-MLL interaction. Also disclosed are methods for treating such leukemias using inhibition of Menin-MLL interaction in combination with DOT1L inhibition.

13 Claims, 10 Drawing Sheets
Specification includes a Sequence Listing.

(56) References Cited

OTHER PUBLICATIONS

Borkin, D., et al., "Pharmacologic inhibition of the menin-MLL interaction blocks progression of MLL leukemia in vivo," Cancer Cell, vol. 4, Issue 27, pp. 589-602 (Apr. 13, 2013).
Borkin, D., et al., "Property focused structure-based optimization of small molecule inhibitors of the protein-protein interaction between menin and mixed lineage leukemia (MLL)," J. Med. Chem., vol. 59, No. 3, pp. 892-912 (Jan. 8, 2016).
Claus, C.R., et al., "DOT1L inhibitor EPZ-5676 displays synergistic antiproliferative activity in combination with standard of care drugs and hypomethylating agents in MLL-rearranged leukemia cells," J. Pharmacology and Experimental Therapeutics, vol. 350, No. 3, pp. 646-656 (Jul. 3, 2014).
He, S., et al., "High-affinity small molecule inhibitors of the menin-mixed lineage leukemia (MLL) interaction closely mimic a natural protein-protein interaction," J. Med. Chem., vol. 57, pp. 1543-1556 (Jan. 28, 2014).
Shi, A., et al., "Structural insights into inhibition of the bivalent menin-MLL interaction by small molecules in leukemia," Blood, vol. 120, No. 23, pp. 4461-4469 (Nov. 29, 2012).
Cierpicki et al., "Challenges and opportunities in targeting the menin-MLL interaction," Future Med Chem. Mar. 2014; 6(4): 447-462. (25 pages).
EPO Communication on Patent Application No. 17744904.8 dated Sep. 23, 2020 (3 pages).

* cited by examiner

FIGURE 1
A
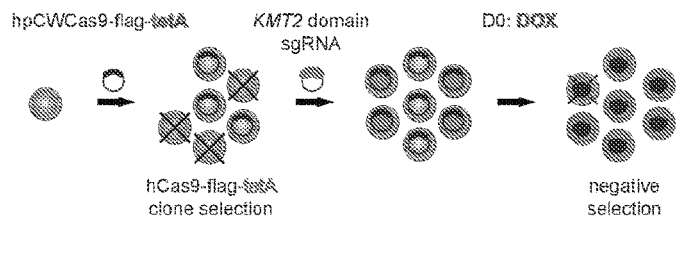
B
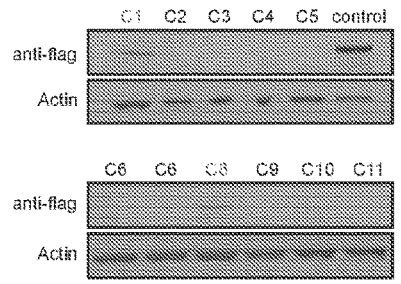
C
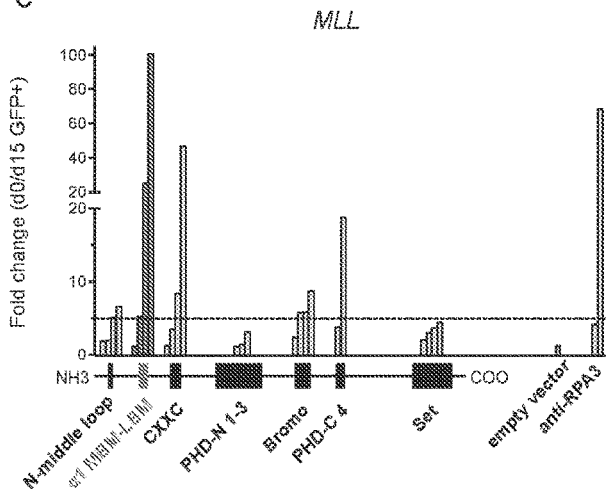
D
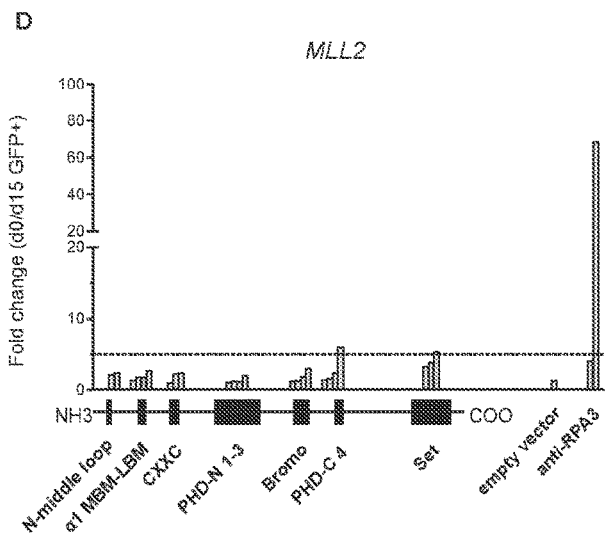
E
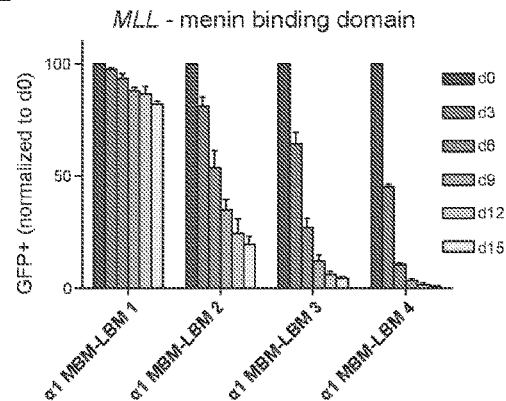
F
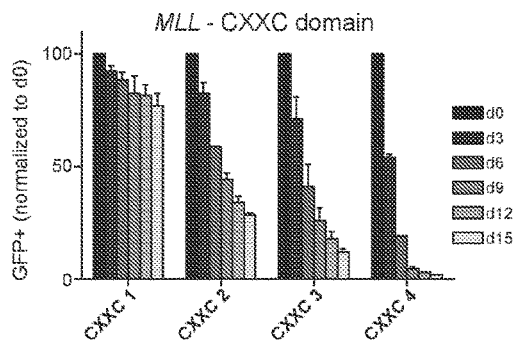

FIGURE 5
A
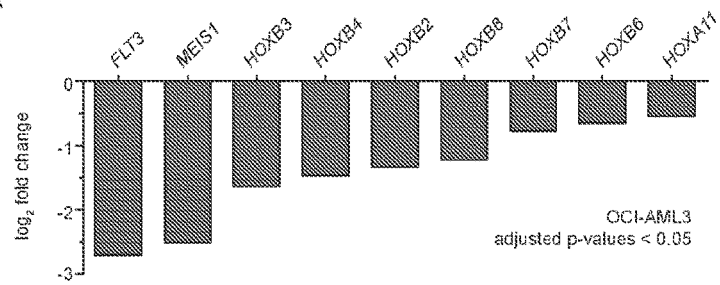
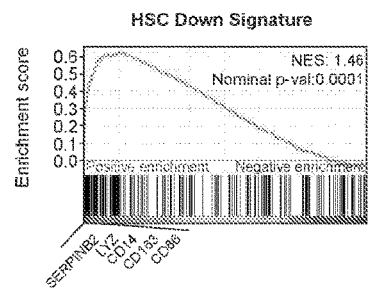
B
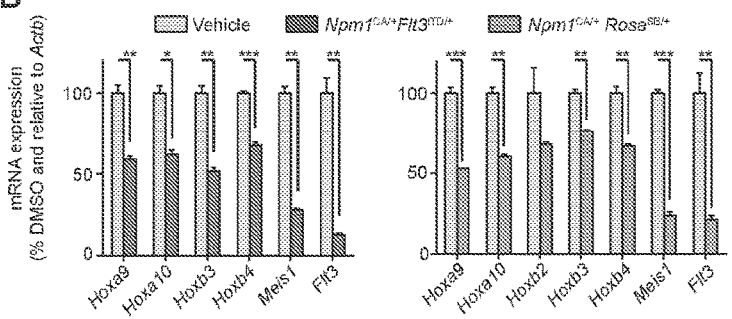
C
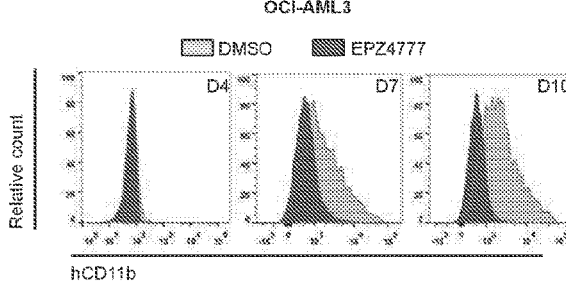
D
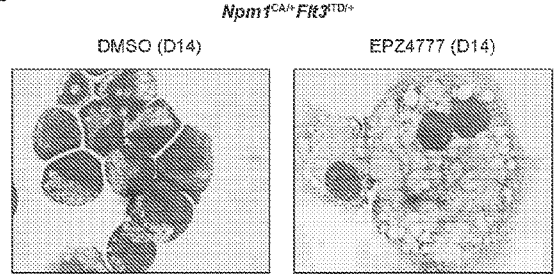
E
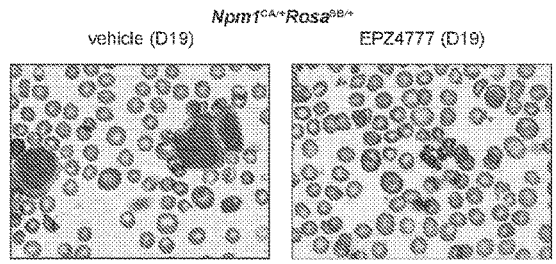
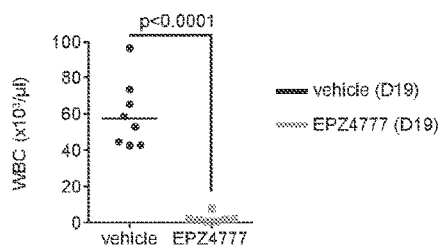
F
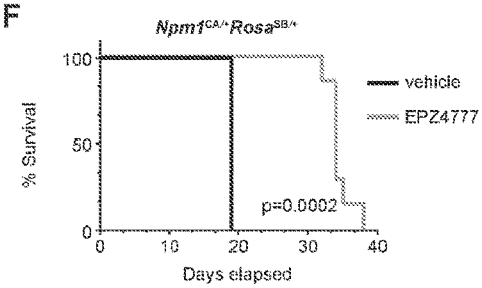

FIGURE 7
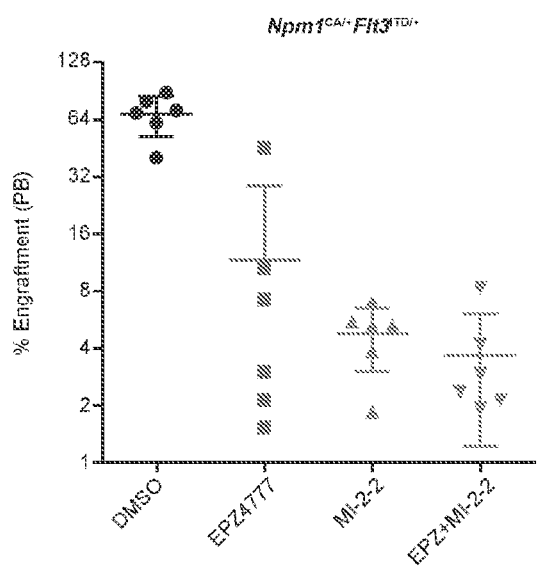
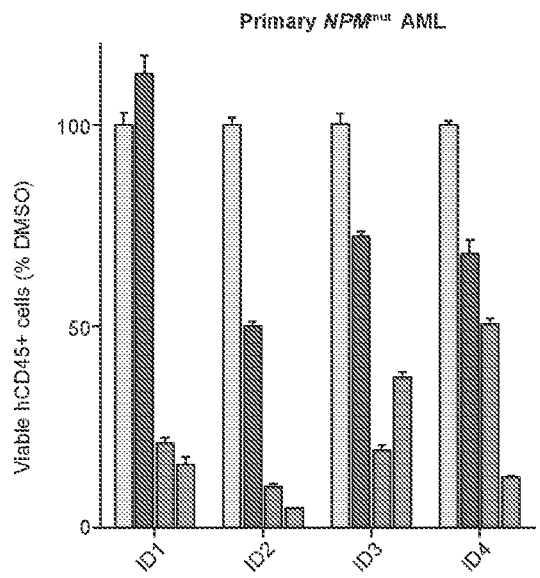

FIGURE 8
A
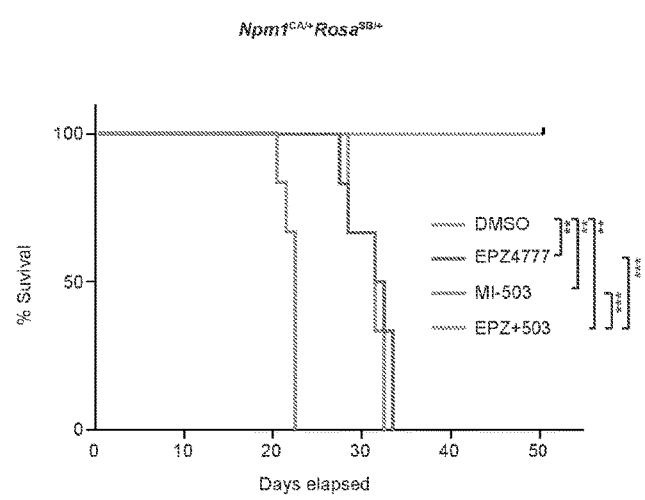
B
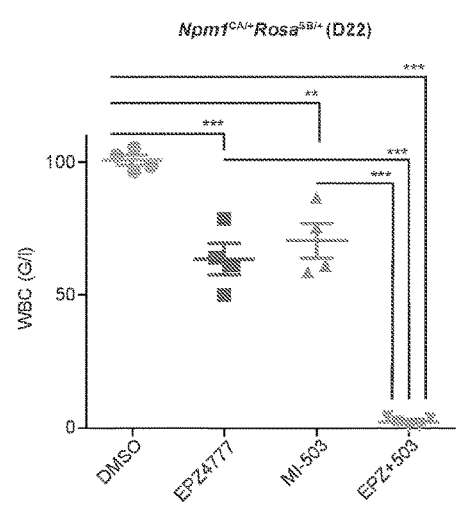

FIGURE 9

Synergy Analysis of $Npm1^{CA/+}FLt3^{ITD/+}$ cells at day 11.

| EPZ4777 | | MI-503 | | EPZ+503 | | |
|---|---|---|---|---|---|---|
| Dose [µM] | Effect | Dose [µM] | Effect | Dose [µM] | Effect | Log(CI)* |
| 10.0 | 0.49 | 2.5 | 0.86 | 12.5 | 1.00 | n.a. |
| 5.0 | 0.48 | 1.25 | 0.66 | 6.25 | 0.99 | -1.8579 |
| 2.5 | 0.35 | 0.625 | 0.52 | 3.125 | 0.91 | -1.6869 |
| 1.25 | 0.30 | 0.3125 | 0.33 | 1.5625 | 0.68 | -0.5569 |
| 0.625 | 0.27 | 0.15625 | 0.20 | 0.78125 | 0.47 | -0.3555 |
| 0.3125 | 0.23 | 0.07813 | 0.16 | 0.39063 | 0.31 | -0.2800 |
| 0.15625 | 0.15 | 0.03906 | 0.13 | 0.19531 | 0.25 | -0.2728 |

Log(CI)=Logarithmic combination index; logarithmic values below 0 indicate synergism;
Effect=Relative growth inhibition

Figure 10

Synergy Analysis of OCI-AML3 cells (day7)

| EPZ4777 | | MI-2-2 | | EPZ+MI-2-2 | | |
|---|---|---|---|---|---|---|
| Dose [µM] | Effect | Dose [µM] | Effect | Dose [µM] | Effect | Log(CI)* |
| 10.0 | 0.82252 | 12 | 0.76 | 22 | 0.94 | -0.0821 |
| 5.0 | 0.7787 | 6 | 0.68 | 11 | 0.97 | -0.5495 |
| 2.5 | 0.74626 | 3 | 0.49 | 5.5 | 0.96 | -0.8043 |
| 1.25 | 0.69816 | 1.5 | 0.24 | 2.75 | 0.92 | -0.8069 |
| 0.625 | 0.61478 | 0.75 | 0.11 | 1.375 | 0.81 | -0.6644 |
| 0.3125 | 0.46254 | 0.375 | 0.06 | 0.6875 | 0.57 | -0.3210 |
| 0.15625 | 0.30157 | 0.1875 | 0.05 | 0.34375 | 0.40 | -0.2047 |

Log(CI)=Logarithmic combination index; logarithmic values below 0 indicate synergism;
Effect=Relative growth inhibition

SEQUENCE LISTING

```
<160> NUMBER OF SEQ ID NOS: 65

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgccccgcgg caacgcgtcc cgg                                                23
```

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggccgccac cgccgaccgg ggg                                           23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgaagacgag gcggacgacg agg                                           23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgacgaagac gaagacgagg cgg                                           23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgcagcgccg cgtcgaagcc cgg                                           23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaccaacct gcgccggttc cgg                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgcaggtct cggccgccat cgg                                           23

<210> SEQ ID NO 8
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggtgggcccg ggcttcgacg cgg                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gacgtcgatc gaggcggtgt ggg                                               23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tatattgcga ccaccaaact tgg                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcttagata agcccaagtt tgg                                               23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtacaaacac cacagtcctc agg                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agaggagaac gagcgccctc tgg                                               23

<210> SEQ ID NO 14
<211> LENGTH: 23
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgcaaattct gtcacgtttg tgg                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actcagggtg atagctgttt cgg                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgtgagacag caacccacgg tgg                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acacatgaag tgatagttgc tgg                                              23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccatttgcta cgctaccggc agg                                              23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtctcgggat ttaagtctgg agg                                              23

<210> SEQ ID NO 20
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 20
tggtggatca ggtccttcgg ggg                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagcagcctt tagatctaga agg                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatggagcgg atgacgttgc cgg                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaagacccc ggccatggat ggg                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggaaaagtat tacgacagca agg                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gagatggtga ttgagtatgc cgg                                              23

<210> SEQ ID NO 26
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 26
ccccgttgcc ccgtccgccg cgg                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caacggggcc gaaagagtgc ggg                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acggccctgc tccgtttgct ggg                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtttgctgg ggctccgccg ggg                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gagccccagc aaacggagca ggg                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggccgtgtcc tccccgggct cgg                                              23

<210> SEQ ID NO 32
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 32
aagatgcgca tggctcgatg tgg                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcggggctgc ctacgtgtgc agg                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtgttaggg cccccaaact tgg                                              23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagctcgtgg agtcctttgc tgg                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agcaccaggt gtcgtgatgc tgg                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccacgcgcaa acggcgccac tgg                                              23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 38
tgcataccac ccggcctgtc tgg                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agtgcgcaca gtgcgatcac tgg                                              23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcatagcagc gtgtacagat cgg                                              23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctggtcggcg gaagtcttcg agg                                              23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctgaagcctg gcgccacggt ggg                                              23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agctgtgagt cagcgcttcg agg                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actcacagct tgcaggccgc agg                                               23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gatgggaagc aactgcaccc agg                                               23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cagcagtggg cccaccacct tgg                                               23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taagcgcaac atcgacgcgg ggg                                               23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cgggtgctat atgttccgca tgg                                               23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggcggcattg ccatgcatcg tgg                                               23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
gggagacggg agagtacaga                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cccgagctga tgagcgagtc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agagagtccc catacgcttg                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gatcgtaaaa atcgccgaga                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
atccagctgc agagaaaagc                                               20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggctccctac cagcagaac                                                19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```
aggttttggg agaacgtgtg                                              20

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgtagcacag cttctcctta atgtc                                        25

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gctctacgat ggggtttgtt                                              20

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gccaaattat cccacaacaa tgtc                                         24

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
attttgggag ggggagattt                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgtcaactcc ccaaaaccat                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

```
gttaggttac tggcgggttg                                               20

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaataggctc tggcgttgc                                                19

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttagcac ttcgcaggag                                               20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agcgcggcta cagcttca                                                 18
```

TARGETING CHROMATIN REGULATORS INHIBITS LEUKEMOGENIC GENE EXPRESSION IN NPM1 MUTANT LEUKEMIA

RELATED APPLICATIONS

This application is a National Stage Application of PCT/US2017/015168, filed Jan. 26, 2017, which claims the priority of U.S. Provisional Application No. 62/287,419, filed Jan. 26, 2016, and also of U.S. Provisional Application No. 62/370,670, filed Aug. 3, 2016. The entire disclosure of each of the prior applications is incorporated by reference.

GRANT SUPPORT

The invention was made with government support under CA 066996 and CA 176745 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 20, 2017, is named 11000-005153-WO0_SL.txt and is 15,516 bytes in size.

BACKGROUND OF THE DISCLOSURE

Field of the Disclosure

The present disclosure relates generally to the treatment of leukemia using pharmacologic inhibition of Menin-MLL interaction. The present disclosure further relates to the treatment of leukemia using inhibition of Menin-MLL interaction in combination with DOT1L inhibition.

Description of the Related Art

The clustered homeobox (HOX) genes are a highly conserved family of transcription factors that are expressed during early development and hematopoiesis[1-3]. Specific members of the HOXA and HOXB cluster are required to maintain self-renewal properties of hematopoietic stem cells (HSCs)[3]. Aberrant HOX gene expression is also a common feature of acute leukemias and believed to play an important role during leukemogenesis[3, 4]. In murine leukemia models aberrant HOX gene expression has been shown to be a critical component of a specific oncogenic gene expression program that can be driven by various oncogenes[3,4]. Retrovirally induced overexpression of specific HOX genes in early hematopoietic progenitors induces leukemia in mice[5]. In human acute myeloid leukemia (AML) aberrant HOX gene expression can be found in 40-60% of cases, but the HOX expression pattern among AML cases is heterogenous and has been used to categorize this disease into four main groups that correlate with the presence of specific molecular markers[4]. Simultaneous expression of the HOXA and HOXB cluster represents the most common patterns in AML and cases within this group frequently carry NPM1 mutations[4, 6, 7].

NPM1 is one of the two most frequently mutated genes in AML (30%) and co-occurs commonly with other mutations such as FLT3, DNMT3A, IDH1, IDH2, and TET2[8-10]. Of these, FLT3 is of particular importance in NPM1$^{mut}$ AML as it is a) the most commonly co-mutated gene with NPM1 and b) an important prognostic marker in these leukemias. Whereas NPM1$^{mut}$ AML lacking a FLT3-ITD is considered a relatively favorable genotype with overall survival rates of up to 60% in younger patients, the presence of a concurrent FLT3-ITD (30% of the cases) converts this genotype into an adverse category[9, 11-13]. Whereas novel small molecule FLT3 inhibitors have clinical activity against FLT3 mutated AML and were recently introduced into current treatment regimens, resistance via acquisition of mutations or subsequent up-regulation of FLT3 transcript levels gene occurred frequently and quickly in first clinical trials. Independent of FLT3 mutation status, survival rates in patients over 65 years of age are even more dismal and only a minority of these patients achieves a sustainable remission[14]. These data highlight the need for novel molecular mechanism-based therapeutic concepts which may be less toxic and more efficacious.

NPM1 is an intracellular chaperone protein implicated in multiple cellular processes, such as proliferation, ribosome assembly, nucleosome assembly and many others[15, 16]. Despite the discovery of NPM1 mutations more than a decade ago, how NPM1 mutations initiate and maintain AML remains unclear thus hindering the development of targeted therapeutic approaches. Also, it is unknown what drives aberrant HOX gene expression and whether these genes are required for NPM1$^{mut}$ leukemogenesis.

Current knowledge of aberrant HOX gene regulation in leukemias has mainly come from studies of MLL-rearranged leukemias. In these leukemias, the mixed-lineage leukemia gene (MLL, also known as KMT2A) is fused to one of more than 60 different fusion partners resulting in the formation of an oncogenic fusion protein[17]. All MLL-rearranged leukemias exhibit aberrant HOXA cluster expression that is dependent on chromatin binding of the MLL-fusion complex[18], which in turn requires the association with at least two other proteins, menin and LEDGF. Whereas menin facilitates LEDGF binding to the complex, the latter directly conveys chromatin binding of MLL[19, 20]. Menin, the protein encoded by the multiple endocrine neoplasia 1 gene (MEN1), is of particular interest as it has been shown to be therapeutically targetable. Recently developed inhibitors of the menin-MLL interaction were demonstrated to have antileukemic activity in preclinical MLL-rearranged leukemia models[21, 22].

The histone 3 lysine 79 (H3K79) methyltransferase DOT1L is another protein of therapeutic interest involved in HOXA cluster regulation of MLL-rearranged leukemias[23-25]. DOT1L is believed to be recruited to promoters of HOXA cluster genes via the MLL fusion partner that is commonly part of the DOT1L binding complex[26]. Small molecule inhibitors of DOT1L were proven to have activity against preclinical models of MLL-rearranged leukemias[27, 28], and are currently being tested in a clinical trial with promising first results presented at (NCT01684150). See, clinicaltrials.gov/ct2/show/NCT01684150.

While it may seem unlikely for these findings to be easily transferable to other HOX expressing leukemias lacking an MLL-fusion protein, it has been shown that the wt-MLL complex and menin[29, 30] are both required for HOXA cluster expression during normal hematopoiesis. In addition, higher states of H3K79 methylation, such as di- and trimethylation (me2 and me3) at the HOX locus are associated with high expression levels of these genes in lineage, Sca-1$^+$, c-Kit$^+$ (LSK) murine hematopoietic progenitors and are converted into monomethylation (me1) as these cells mature into more committed progenitors lacking HOX expression[24]. Whether HOXB cluster expression in LSKs is also associated with H3K79me2 and me3 is unknown to date.

The applicant has previously proposed to use DOT1L inhibition in the treatment of leukemias that are not characterized by MLL-translocation or MLL-rearrangement or MLL-partial duplication. See, U.S. Pat. No. 10,407,732 (371 application of PCT/US2014/049641 filed on Aug. 4, 2014 and published as WO/2015/017863) and incorporated by reference in its entirety for all purposes.

While NPM1$^{mut}$ AML without concurrent FLT3-ITD is being considered a relatively favorable subtype, only about half of the younger patients with NPM1 mutations achieve long-term disease-free survival following current treatment approaches[9, 11, 12, 37]. Outcome in patients >65 years of age is generally poor[14]. These numbers indicate the demand for more efficacious and potentially less toxic therapies. Research efforts within the last years led to important findings describing distinctive biological features of NPM1$^{mut}$ AML such as a HOX gene dominated expression signature[4, 6] and lack of CD34 expression in the majority of cases[38]. Also, it is known for more than a decade that the NPM1 mutations results in cytoplasmic dislocation of the mutant protein[8]. However, it is still incompletely understood how aberrant HOX gene expression is maintained and what mechanisms specifically drive leukemic transformation[3]. While HOX and MEIS1 transcription factors have thus far not proven to be amenable for pharmacological inhibition, current efforts to develop drugs that directly target the mutant NPM1 protein or restore its physiological cellular localization have been largely unsuccessful or of controversial therapeutic benefit as currently discussed for all-trans-retinoic acid[39-41].

Molecularly targeted drug development has consequently been challenging for NPM1$^{mut}$ AML. A better understanding of biological processes involved in NPM1$^{mut}$ leukemogenesis would therefore facilitate the definition of molecular targets suitable for pharmacological inhibition. Thus, an acute need remains for provision of novel therapies against leukemias.

BRIEF DESCRIPTION OF THE DRAWINGS

FIGS. 1A-F are schematics, graphs, and blots showing CRISPR-Cas9 mutagenesis of exons targeting MLL protein domains in NPM1$^{mut}$ AML cells (FIG. 1A) Experimental strategy for CRISPR-Cas9 negative selection screening: Engineering of a clonal NPM1$^{mut}$ OCI-AML3 cell line that expresses a human codon-optimized Cas9 (hpCW-Cas9-flag-tetA) vector containing a puro resistance gene (p), a flag-tagged (flag) and tetracycline-inducible (tetA) Cas9). GFP reporters of sgRNA constructs were used to track sgRNA negative selection after doxycycline induction of Cas9 (D0, day 0; DOX, doxycycline). (FIG. 1B) Immunoblotting for flag-tagged hCas9 after tetracycline treatment in eleven OCI-AML3-Cas9 single cell clones. C1 and C8 clones were selected for two independent screens of MLL and MLL2.

(FIG. 1C and FIG. 1D) represent a summary of results of negative selection experiments with sgRNAs targeting exons encoding for specific MLL or MLL2 protein domains. Negative selection is plotted as the fold depletion of GFP$^+$ cells (d0 GFP % divided by d15GFP %) during 18 days in culture. Each bar represents an independent sgRNA. The location of each sgRNA relative to the MLL or MLL2 protein is indicated along the x axis. The dashed line indicates a fivefold change. The data shown are the mean value of two independent replicates. Empty vector and anti-RPA3 sgRNA guides represent negative and positive controls. (FIGS. 1E+F) Negative-selection competition assay that plots the percentage of GFP cells over time following transduction of OCI-AML3-Cas9 with the indicated sgRNAs. GFP$^+$ percentage is normalized to the day 0 measurement following doxycycline induction of Cas9 (3 days after sgRNA transduction). N-middle loop, N-terminal middle loop of the menin-binding; alpha MBM-LBM, left part of the menin binding domain; CXXC, CXXC-type zink finger domain; PHD-N 1-3, N-terminal plant homeodomains 1-3; Bromo, bromodomain; PHD-C 4, C-terminal plant homeodomain 4; Set, SET-domain. (Error bars represent standard error of the mean).

(FIG. 2A) Dose response curves from cell viability assays after 11 days of MI-2-2 and MI-503 treatment. (FIG. 2B) HOX gene expression in the human OCI-AML3 cells following four days of MI-2-2 treatment (12 µM). (FIG. 2C) MI-503 (2.5 µM) treatment of murine Npm1$^{CA/+}$Rosa$^{SB/+}$, Mll-Af9, and Hoxa9-Meis1-transformed cells in colony forming assays assessed on d7 and d14. (FIG. 2D) Gene expression in murine Npm1$^{CA/+}$Flt3$^{ITD/+}$ and Npm1$^{CA/+}$Rosa$^{SB/+}$ cells assessed on day 4 of MI-503 treatment (2.5 µM). (FIG. 2E) Dose response curves from cell viability assays after 11 days of MI-503 treatment comparing Npm1$^{CA/+}$Flt3$^{ITD/+}$ cells versus Npm1$^{CA/+}$Flt3$^{ITD/+}$ cells overexpressing Hoxb4, Meis1, or Hoxa9-Meis1. (FIG. 2F) Cell differentiation upon menin-MLL-inhibition (MI-2-2: 12 µM; MI-503 2.5 µM) as determined by CD11b expression in OCI-AML3 cells (at day 0, 4, and 7 of treatment) and morphological changes consistent with granulocytic monocytic differentiation in murine Npm1$^{CA/+}$Rosa$^{SB/+}$ cells after 7 days of MI-503 treatment. (FIG. 2G) Assessment of leukemia burden in OCI-AML3 xenotransplantation model after 7 days of MI-503 in vivo treatment as determined by human CD45 positive cells in the murine bone marrow. (FIG. 2H) Gene expression changes after 7 days of MI-503 in vivo treatment. (FIG. 2I) Kaplan-Meier survival curves of vehicle and MI-503 treated NSG mice xenotransplanted with 5×10E6 OCI-AML3 cells (n=4 mice per group). (Error bars represent standard error of the mean).

(FIG. 3A) Relative enrichment of menin at selected HOXA, HOXB, and MEIS1 gene loci (TSS) in OCI-AML3 cells upon 5 days of menin inhibition (MI-503, 2.5 µM) compared to drug vehicle as assessed by ChIP with a menin-specific antibody followed by qPCR. Immunoblotting of indicated chromatin marks following 4 days of MI-503 treatment (2.5 µM). (FIG. 3B) Global levels of indicated chromatin marks after 4 days of MI-503 (2.5 µM) versus DMSO. (FIGS. 3C+D) H3K4me3 and H3K79me2 enrichment across the HOX gene locus and at MEIS1 following 4 days of MI-503 treatment (2.5 µM) versus DMSO.*p<0.05, p<0.005, *p<0.0005. Errors bars represent standard error of the mean.

(FIG. 4A) Expression of Hoxa9, Meis1, Hoxb2, Hoxb3, and Hoxb4 in LSKs sorted from Dot1l$^{fl/fl}$ or Dot1l$^{WT/WT}$ mice crossed with Mx1-Cre mice treated with pIpC 10 days before. The box plot shows normalized expression values from six independent replicates. Whiskers represent the upper and lower limits of the range. Boxes represent the first and third quartiles, and the line represents the median.

*p<0.05. (FIG. 4B) Representative profiles for ChIP-seq using anti-H3K79me1, H3K79me2, H3K79me3, and H3K27me3 antibodies in LSK cells at the HOXA and HOXB cluster. The y axis scale represents read density per million sequenced reads. (FIG. 4C) Growth of OCI-AML3, MOLM-13, SET2, OCI-AML2, and HL-60 cells exposed to 10 µM EPZ4777. Viable cells were counted and re-plated at equal cell numbers in fresh media with fresh compound every 3-4 days. Results were plotted as percentage of split-adjusted viable cells in the presence of 10 µM EPZ4777 and normalized to DMSO vehicle control. Data represent mean values of biological triplicates. (FIG. 4D) Colony numbers of $Npm1^{CA/+}Flt3^{ITD/+}$, $Npm1^{CA/+}Rosa^{SB/+}$, Mll-Af9, and Hoxa9-Meis1 cells exposed to 10 µM EPZ4777 and compared to DMSO vehicle control. Data were obtained at day 7 (D7), when viable cells were harvested and replated in fresh methylcellulose with fresh compound and at day 14 (D14) of treatment and represent mean of biological triplicates. (FIG. 4E) Immunoblotting of global chromatin marks in OCI-AML3 cells upon 4 days of EPZ4777 treatment (10 µM). (FIG. 4F) H3K79me2 levels across the HOXA and HOXB cluster locus and MEIS1 in OCI-AML3 cells after 4 and 7 days of EPZ4777 (10 µM) treatment and compared to DMSO vehicle control as assessed by ChIP-PCR. (Error bars represent standard error of the mean).

FIGS. 5A-F are graphs and images showing effects of DOT1L inhibition on gene expression, cell differentiation and leukemia initiating potential in $NPM^{mut}$ AML cells. (FIG. 5A) (Left panel) $Log_2$ fold change of HOX genes, MEIS1, and FLT3 between OCI-AML3 cells treated for 7 days with 10 µM EPZ4777 or DMSO vehicle control as assessed by RNA-sequencing. Only expressed HOXA and HOXB cluster genes were shown that had a normalized read count of at least 100 reads within the vehicle control and showed at least a 0.5 log 2 fold change. Data shown represent mean of biological triplicates and p-values adjusted for multiple testing were at least <0.05. (Right panel) Gene set enrichment analysis of RNA sequencing data reveals that genes upregulated after 7 days of EPZ4777 treatment were enriched for genes that have been shown to be silenced in normal hematopoetic cord blood stem cells. (FIG. 5B) Gene expression in murine $Npm1^{CA/+}Flt3^{ITD/+}$ and $Npm1^{CA/+}Rosa^{SB/+}$ cells assessed on day 7 of EPZ4777 treatment (10 µM) by quantitative PCR. Values represent mean±SEM of biological triplicates. (FIG. 5C) Cell differentiation upon DOT1L inhibition (EPZ4777, 10 µM) as determined by flow cytometry for CD11b expression in OCI-AML3 cells (at day 0, 4, and 7 of treatment). (FIG. 5D) Morphological changes in $Npm1^{CA/+}Flt3^{ITD/+}$ consistent with monocytic differentiation in murine cells after 14 days of EPZ4777 treatment at 10 µM. (FIG. 5E) Morphology (upper panel) and white blood cell count (lower panel) of mice transplanted with pretreated $Npm1^{CA/+}Rosa^{SB/+}$ leukemia cells on day 19 post transplantation. (FIG. 5F) Kaplan-Meier survival curve of mice transplanted with pretreated $Npm1^{CA/+}Rosa^{SB/+}$ leukemia cells.

(FIG. 6A) Dose response curves from cell viability assays of OCI-AML3 cells comparing 7 days of MI-2-2, EPZ4777 and combinatorial EPZ4777 and MI-2-2 (EPZ+2-2) treatment. Values represent mean±SEM of biological triplicates. (FIG. 6B) Dose response curves from cell viability assays of $Npm1^{CA/+}Flt3^{ITD/+}$ leukemia cells comparing 11 days of MI-503, EPZ4777 and combinatorial EPZ4777 and MI-503 (EPZ+503) treatment. Values represent mean±SEM of biological triplicates. (FIG. 6C) Comparison of MI-503 (2.5 µM), EPZ4777 (10 µM), and combinatorial MI-503 and EPZ4777 treatment of murine $Npm1^{CA/+}Rosa^{SB/+}$ leukemia cells in colony forming assays assessed on day 7 and day 14 of treatment. Data were obtained at day 7 (D7), when viable cells were harvested and replated in fresh methylcellulose with fresh compound and at day 14 (D14) of treatment and represent mean±SEM of biological triplicates. (FIG. 6D) Pictures of representative colonies from cells $Npm1^{CA/+}Rosa^{SB/+}$ leukemia cells following 7 days of EPZ4777 (10 µM), MI-503 (2.5 µM) or combinatorial EPZ4777 and MI-503 treatment. (FIG. 6E) Gene expression changes in human OCI-AML3 following 4 days of EPZ4777 (10 µM), MI-2-2 (12 µM) or combinatorial EPZ4777 and MI-2-2 treatment as assessed by quantitative PCR. Values represent mean±SEM of biological triplicates. The most significant three genes of Hoxa and Hoxb cluster, Meis1, and Flt3 are shown. Values represent mean±SEM of biological triplicates. (FIG. 6F) Gene expression changes in murine $Npm1^{CA/+}Rosa^{SB/+}$ (left panel) and $Npm1^{CA/+}Flt3^{ITD/+}$ leukemia cells (right panel) following 4 days of EPZ4777 (10 µM), MI-503 (2.5 µM) or combinatorial EPZ4777 and MI-503 treatment as assessed by quantitative PCR. Values represent mean±SEM of biological triplicates. The most significant three genes of Hoxa and Hoxb cluster, Meis1, and Flt3 are shown. Values represent mean±SEM of biological triplicates. (FIG. 6G) Apoptosis in OCI-AML3 cells following 4 days of EPZ4777 (10 µM), MI-2-2 (12 µM) or combinatorial EPZ4777 and MI-2-2 treatment as assessed by flow-cytometric staining for Annexin V. (FIG. 6H) Cell differentiation of $NPM1^{mut}$ leukemia cells as assessed by flow cytometric analysis of CD11b in OCI-AML3 cells (upper panel) and by morphological analysis of cytospins of $Npm1^{CA/+}Rosa^{SB/+}$ leukemia cells (lower panel). Representative pictures are shown in the lower panel and data were obtained for both analyses after 4 days of treatment.

FIGS. 7A-B are graphs showing effects of single and combined menin-MLL and DOT1L inhibition in vivo and on primary $NPM1^{mut}$ AML patient samples. (FIG. 7A) Engraftment values in the peripheral blood after 54 days following transplantation of pretreated $Npm1^{CA/+}Flt3^{ITD/+}$ leukemia cells comparing drug vehicle, EPZ4777, MI-2-2, and combinatorial EPZ4777 and MI-2-2 inhibition. Engraftment was determined by positivity for both CD45.1 and CD45.2 expression using flow cytometry (host CD45.1 only). Values represent mean±SEM. (FIG. 7B) Viable cell numbers of 4 independent samples of de novo $NPM1^{mut}$ AML treated in co-culture assays with DMSO, EPZ4777 (10 µM), MI-503 (2.5 µM), or combinatorial EPZ4777 and MI-503. Values represent mean±SEM of biological triplicates.

FIGS. 8A-B are graphs showing effects of single and combinatorial menin-MLL and DOT1L inhibition in vivo. (FIG. 8A) Kaplan—Meier survival curve of mice transplanted with pretreated $Npm1^{CA/+}Rosa^{SB/+}$ leukemia cells comparing drug vehicle, EPZ4777, MI-503, or combinatorial EPZ4777 and MI-503 inhibition. (FIG. 8B) Engraftment values in the peripheral blood 22 days after transplantation of pretreated $Npm1^{CA/+}Rosa^{SB/+}$ leukemia cells comparing drug vehicle, EPZ4777, MI-2-2, and combinatorial EPZ4777 and MI-503 inhibition.

FIG. 9 is a table showing synergy analysis of $Npm1^{CA/+}FLt3^{ITD/+}$ cells at day 11.

FIG. 10 is a table showing synergy analysis of OCI-AML3 cells at day 7.

SUMMARY OF THE DISCLOSURE

Figure 2:
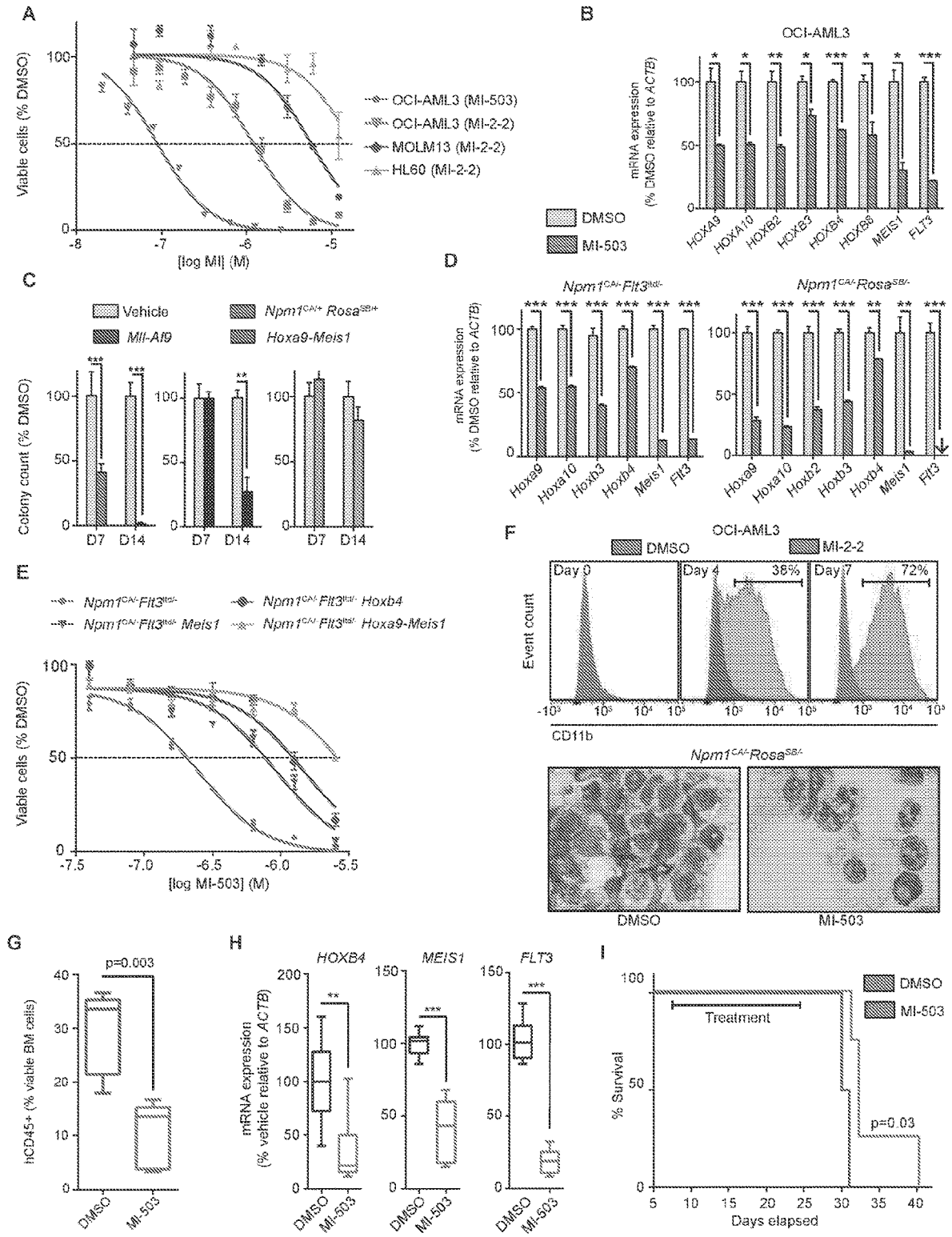
FIGS. 2A-I are graphs and images showing effects of menin-MLL inhibition in human and murine NPM1$^{mut}$ leukemia cells in vitro and in vivo.

The inventors hypothesized that aberrant HOX and MEIS1 gene expression in $NPM1^{mut}$ AML might be driven by similar mechanisms that control these genes in normal HSCs and that high expression of FLT3, a reported downstream target of MEIS1, is indirectly driven via elevated MEIS1 transcript levels. Using CRISPR-Cas9 genome editing and small molecule inhibition, the inventors identified the chromatin regulators MLL and DOT1L as therapeutic targets that control HOX MEIS1 and FLT3 expression and differentiation in NPM1$^{mut}$ leukemia.

The inventors first conjectured MLL to be also involved in controlling HOX gene expression in NPM1$^{mut}$ AML. Using a CRISPR-Cas9 negative selection screen targeting multiple MLL protein domains, the inventors discovered the menin binding site of MLL as a top hit in their screen. Additionally, the inventors detected a strong phenotype for at least one of the sgRNAs targeting the CXXC domain, again pointing to chromatin binding of MLL being critically required for NPM1$^{mut}$ leukemias[48]. Of note, none of the sgRNAs targeting the C-terminal SET domain of MLL—that contains the H3K4 methyltransferase activity but is always lost in MLL-fusion proteins[17]—exhibited any significant phenotype.

In one aspect of the present disclosure, a method for inhibiting proliferation of or inducing apoptosis in a leukemia cell, or for both inhibiting proliferation and inducing apoptosis in the cell is provided, wherein the method comprises contacting said leukemia cell with an inhibitor of interaction between MLL and menin, wherein said leukemia cell exhibits an NMP1 mutation.

In further embodiments, the NPM1 mutation exhibiting leukemia cell is selected from the group consisting of an acute lymphocytic leukemia (ALL) cell and an acute myeloid leukemia (AML) cell.

In other embodiments, the inhibitor of interaction of MLL and menin inhibits the interaction with an IC50 of from about 100 nM to about 10 µM or from about 250 nM to about 5 µM or from about 500 nM to about 1 µM.

In more specific embodiments, the inhibitor of interaction of MLL and menin is selected from the group consisting of MI-0202, MI-503, MI-463, MI-136, ML-225, the compounds in Table 2 of the present application, a compound of the formula:

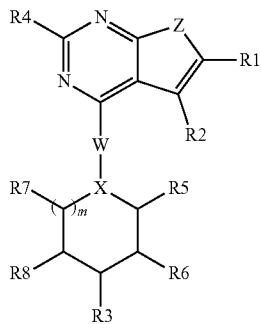

wherein R1, R2, R3, R4, R5, R6, R7, and R8 are each independently selected from the group consisting of H, substituted or non-substituted alkyl, substituted or non-substituted alkoxy, a halogen (e.g. F, Cl, Br, I, and At), a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; Z is S or O or NH or CH—CH; W is present or absent and is NH or NH—(CH$_2$)$_n$ (n is an integer between 0 and 10), or (CH$_2$)$_n$ (n is an integer between 0 and 10) or O or O—(CH$_2$)$_n$ (n is an integer between 0 and 10); X and Y are each independently N or C; and m is an integer between 0 and 3 or pharmaceutically acceptable salts of thereof: or a compound of the formula:

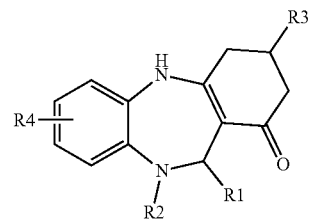

wherein R1, R2, R3, and R4 are each independently selected from the group consisting of: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused to the benzodiazepine ring system non-substituted or substituted with alkyl, aryl, halogen, hydrogen bond donor or acceptor, carbocyclic or heterocyclic aromatic ring comprising carbon; or pharmaceutically acceptable salts thereof.

In another aspect of the disclosure, a method for treating a patient afflicted with a leukemia, is provided wherein the method comprises:

administering to said patient an inhibitor of interaction between MLL and menin, in an amount effective to inhibit proliferation and/or enhance apoptosis of leukemic cells of the patient;

said patient being afflicted with a leukemia that exhibits an NPM1 mutation.

In more specific embodiments, the method further comprises testing a leukemia tissue sample or cell obtained from the patient for the presence of said NMP1 mutation and (i) proceeding with the administration if the patient is determined to possess said mutation; or (ii) conversely, not proceeding with the administration if the patient is determined to lack said mutation.

In some embodiments, the leukemia is selected from the group consisting of an acute lymphocytic leukemia (ALL) and an acute myeloid leukemia (AML).

In some embodiments, the inhibitor of interaction between MLL and menin inhibits the interaction with an IC50 of from about 100 nM to about 10 μM or from about 250 nM to about 5 μM or from about 500 nM to about 1 μM.

In more specific embodiments, the inhibitor of interaction between MLL and menin is selected from the group consisting of MI-0202, MI-503, MI-463, MI-136 and ML-225, a compound disclosed in Table 2 of the specification, and pharmaceutically acceptable salts or free base versions thereof or a compound of the formula:

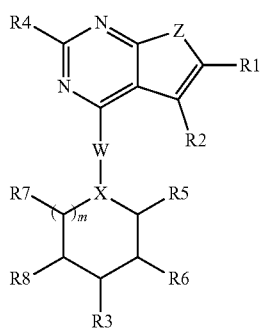

wherein R1, R2, R3, R4, R5, R6, R7, and R8 are each independently selected from the group consisting of: H, substituted or non-substituted alkyl, substituted or non-substituted alkoxy, a halogen (e.g. F, Cl, Br, I, and At), a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more of nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; Z is S or O or NH or CH—CH; W is present or absent and is NH or NH—$(CH_2)_n$ (n is an integer between 0 and 10), or $(CH_2)_n$ (n is an integer between 0 and 10) or O or O—$(CH_2)_n$ (n is an integer between 0 and 10); X and Y are each independently N or C; and m is an integer between 0 and 3; or pharmaceutically acceptable salts of thereof; or a compound of the formula:

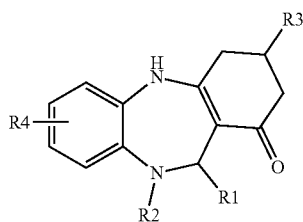

wherein R1, R2, R3, and R4 are each independently selected from the group consisting of: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused to the benzodiazepine ring system non-substituted or substituted with alkyl, aryl, halogen, hydrogen bond donor or acceptor, carbocyclic or heterocyclic aromatic ring comprising carbon; or pharmaceutically acceptable salts thereof.

In yet another aspect of the present disclosure, a method for treating leukemia in a patient previously identified as afflicted by a leukemia exhibiting an NMP1 mutation is provided, the method comprising:

administering to said patient an inhibitor of interaction between MLL and menin in an amount effective to inhibit proliferation and/or enhance apoptosis of leukemic cells of the patient.

In some embodiments of any of the foregoing aspects, there is an additional administration to the patient a DOT1L inhibitor in at least an amount effective, in combination with the MLL-menin interaction inhibitor, to inhibit proliferation and/or enhance apoptosis of leukemic cells of the patient.

In more specific embodiments, the DOT1L inhibitor inhibits DOT1L with an IC50 of from about 100 nM to about 10 μM or from about 250 nM to about 5 μM or from about 500 nM to about 1 μM.

In some embodiments of any of the foregoing aspects and embodiments, the inhibitor of interaction of MLL and menin is provided at a dosage of at least about 2 mg inhibitor/m2/day or at least about 10 mg inhibitor/m2/day or at least about 20 mg inhibitor/m2/day or at least bout 50 mg inhibitor/m2/day or at least about 100 mg inhibitor/m2/day or at least about 200 mg inhibitor/m2/day or at least about 500 mg inhibitor/m2/day or maximum tolerated dose if lower.

In some embodiments involving dual administration, the amount of at least one of the inhibitors is the same as it would have been had the at least one inhibitor been used alone and not in said combination for achieving the maximum level of proliferation inhibition and/or apoptosis of leukemic cells achievable by using the same inhibitor as monotherapy.

In other embodiments involving dual administration the amount of at least one of said inhibitors is lower than it would have been had the at least one inhibitor been used alone and not in said combination for achieving the maximum level of proliferation inhibition and/or apoptosis of leukemic cells achievable by using the same inhibitor as monotherapy.

In more specific embodiments of the foregoing aspect of the disclosure, the DOT1L inhibitor is selected from the group consisting of a purine, a carbocycle-substituted purine and a 7-deazapurine; in yet more specific embodiments, the DOT1L inhibitor is selected from the group consisting of EPZ00477 and EPZ005676; or from the group consisting of SGC-0946, SYC-522, SYC-534, and SYC-687.

In still another aspect of the present disclosure a method is provided for determining susceptibility of a leukemia patient to treatment with an inhibitor of interaction between MLL and menin alone or in combination with a DOT1L inhibitor, said method comprising:

testing a leukemia tissue sample or cell obtained from the patient for the presence of an NMP1 mutation; and (i) selecting the patient as a candidate for treatment with an inhibitor of interaction of MLL with menin alone or in combination with a DOT1L inhibitor if the sample tests positive for said mutation; or (ii) eliminating the patient as a candidate for said treatment if the sample tests negative for said mutation.

In another aspect, a method is provided for predicting the therapeutic efficacy of an inhibitor of interaction between MLL and menin alone or in combination with a DOT1L inhibitor in a leukemia patient wherein the patient does not exhibit an MLL-translocation, an MLL-rearrangement, and/or an MLL-partial tandem duplication, said method comprising:

testing a leukemia tissue sample or cell from said patient for the presence of an NPM1 mutation, wherein the presence of said mutation in said sample or cell is predictive of the therapeutic efficacy of the inhibitor of MLL-menin interaction alone or in combination with a DOT1L inhibitor in the patient.

In another aspect of the present disclosure a method is provided for inhibiting the proliferation and/or inducing apoptosis of a leukemia cell, said method comprising contacting said leukemia cell with an inhibitor of interaction between MLL and menin, alone or in combination with a DOT1L inhibitor, wherein said leukemia cell exhibits an NPM1 mutation and wherein said cell does not exhibit a genetic mutation, alteration, and/or abnormality that is an MLL-translocation (MLL-t), an MLL-rearrangement (MLL-r), or an MLL-partial tandem duplication (MLL-PTD).

In still another aspect a method for treating a leukemia patient is provided wherein an NMP1 mutation has been identified in a tissue sample or cell of the patient, said method comprising:

administering to said patient one or more inhibitors of interaction between MLL and menin alone or in combination with a DOT1L inhibitor, in amounts individually or combinedly effective in the treatment of leukemia;

wherein the patient does not also exhibit a genetic mutation, alteration, and/or abnormality is selected from the group consisting of an MLL-t, an MLL-r, and/or an MLL-PTD.

In further embodiments of the foregoing aspects including all embodiments thereof, the tissue sample is a blood sample, a bone marrow sample, or a lymph node sample.

23. In more specific embodiments of any of the foregoing aspects including all embodiments thereof, administration of the DOT1L inhibitor in said combination enhances the inhibition of proliferation and/or apoptosis of leukemic cells achieved by administration of the inhibitor of interaction of MLL and menin as monotherapy; in particular embodiments, the enhancement is synergistic, as illustrated without limitation in Examples 11 and more particularly 12.

In a first alternative aspect, a use of an inhibitor of interaction between MLL and menin is provided, in the treatment of leukemia in an amount effective to inhibit proliferation and/or enhance apoptosis of leukemic cells, wherein the leukemia exhibits an NPM1 mutation.

In some embodiments of this alternative aspect, the leukemia has been determined to possess the NPM1 mutation prior to treatment; in particular embodiments, the leukemia is selected from the group consisting of an acute lymphocytic leukemia (ALL) and an acute myeloid leukemia (AML).

In some embodiments of this first alternative aspect, the inhibitor of interaction between MLL and menin inhibits the interaction with an IC50 of from about 100 nM to about 10 μM or from about 250 nM to about 5 μM or from about 500 nM to about 1 μM.

In more specific embodiments of the first alternative aspect, the inhibitor of interaction between MLL and menin is selected from the group consisting of MI-0202, MI-503, MI-463, a compound disclosed in Table 2 of the specification, and pharmaceutically acceptable salts or free base versions thereof or a compound of the formula:

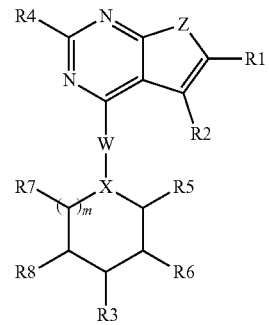

wherein R1, R2, R3, R4, R5, R6, R7, and R8 are each independently selected from the group consisting of: H, substituted or non-substituted alkyl, substituted or non-substituted alkoxy, a halogen (e.g. F, CI, Br, I, and At), a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more of nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; Z is S or O or NH or CH—CH; W is present or absent and is NH or NH—(CH$_2$)$_n$ (n is an integer between 0 and 10), or (CH$_2$)$_n$ (n is an integer between 0 and 10) or O or O—(CH$_2$)$_n$ (n is an integer between 0 and 10); X and Y are each independently N or C; and m is an integer between 0 and 3; or pharmaceutically acceptable salts of thereof; or a compound of the formula:

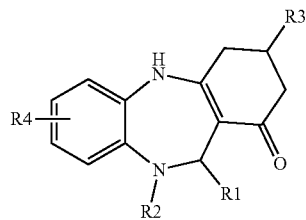

wherein R1, R2, R3, and R4 are each independently selected from the group consisting of: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused to the benzodiazepine ring system non-substituted or substituted with alkyl, aryl, halogen, hydrogen bond donor or acceptor, carbocyclic or heterocyclic aromatic ring comprising carbon; or pharmaceutically acceptable salts thereof.

In a second alternative aspect of the present disclosure, use of an inhibitor of interaction between MLL and menin is provided in an amount effective to inhibit proliferation and/or induce apoptosis of leukemic cells previously identified as exhibiting an NMP1 mutation.

In some embodiments of first or second alternative aspects, the inhibitor of interaction between MLL and menin is used in combination with a DOT1L inhibitor in at least an amount effective, in combination with the MLL-menin interaction inhibitor, to inhibit proliferation and/or enhance apoptosis of leukemic cells of the patient; in more specific embodiments, the DOT1L inhibitor inhibits DOT1L with an IC50 of from about 100 nM to about 10 µM or from about 250 nM to about 5 µM or from about 500 nM to about 1 µM.

In other embodiments of first or second alternative aspects, the amount of at least one of the inhibitors is the same as it would have been had the at least one inhibitor been used alone and not in said combination for achieving the maximum level of proliferation inhibition and/or apoptosis achievable by using the same inhibitor as monotherapy; and in yet other embodiments, the amount of at least one of said inhibitors is lower than it would have been had the at least one inhibitor been used alone and not in said combination for achieving the maximum level of proliferation inhibition and/or apoptosis achievable by using the same inhibitor as monotherapy.

In more specific embodiments of alternative aspects, the DOT1L inhibitor is selected from the group consisting of a purine, a carbocycle-substituted purine and a 7-deazapurine; or the DOT1L inhibitor is specifically selected from the group consisting of EPZ00477 and EPZ005676.

In other specific embodiments of alternative aspects, the DOT1L inhibitor is selected from the group consisting of SGC-0946, SYC-522, SYC-534, and SYC-687.

In more specific embodiments of alternative aspects, the inhibitor of interaction between MLL and menin is selected from the group consisting of MI-0202, MI-503, MI-463, MI-136 and ML-227.

In embodiments of any of the foregoing aspects, MLL is MLL1.

In embodiments of any of the foregoing aspects, the leukemia or cell does not exhibit a genetic mutation, alteration, and/or abnormality that is an MLL-translocation (MLL-t), an MLL-rearrangement (MLL-r), or an MLL-partial tandem duplication (MLL-PTD).

In embodiments of any of the foregoing aspects, the leukemia or cell exhibits a wild type MLL.

In embodiments of any of the foregoing aspects the leukemia or cell does not exhibit a rearranged or fused MLL.

DETAILED DESCRIPTION

In the present disclosure, the inventors have discovered MLL and DOT1L in NPM1$^{mut}$ AML to control HOXA and HOXB cluster and MEIS1 expression on a chromatin level. Based on the observation that the wildtype MLL protein complex is required for HOXgene regulation during normal hematopoiesis[42-47], the inventors first conjectured MLL to be also involved in controlling HOXgene expression in NPM1$^{mut}$ AML. Using a CRISPR-Cas9 negative selection screen targeting multiple MLL protein domains, the inventors discovered the menin binding site of MLL as a top hit in their screen, while it was previously known that the menin-MLL interaction is critically involved in chromatin binding of the MLL complex[19, 20]. Additionally, the inventors detected a strong phenotype for at least one of the sgRNAs targeting the CXXC domain, again pointing to chromatin binding of MLL being critically required for NPM1$^{mut}$ leukemias[48]. Of note, none of the sgRNAs targeting the C-terminal SET domain of MLL—that contains the H3K4 methyltransferase activity but is always lost in MLL-fusion proteins[17]—exhibited any significant phenotype. It has naturally been hypothesized by researchers over decades that MLL family member regulate transcription via H3K4 methyltransferase activity. However, findings of the present disclosure are in line with a recent study on MLL-fusion leukemias in which the remaining wildtype MLL protein was required for leukemic transformation but selective inactivation of the SET domain did neither alter transcription of HOX genes nor transforming potential[49]. In addition, the inventors found no evidence that MLL2, the other MLL family member that interacts with menin and carries a SET domain, is involved in NPM1$^{mut}$ leukemogenesis. Whether HOX gene activation is a direct consequence of MLL chromatin binding itself or dependent on other proteins that are indirectly recruited to chromatin via MLL remains to be determined.

DOT1L is another chromatin modifier that the inventors of the present disclosure discovered to be involved in HOX gene control in NPM1$^{mut}$ leukemias. While it is believed that DOT1L is misdirected to HOXA cluster loci in MLL-fusion leukemias via the fusion partner protein[26], our data do not explain, how DOT1L is misguided to HOXA and B genes and MEIS1 in NPM1$^{mut}$ AML and during normal hematopoiesis. However, we found a clear association of HOXA and HOXB cluster and MEIS1 expression levels in murine LSK cells with higher states of H3K79 methylation. Furthermore, evidenced by the inventor's data from DOT1L$^{fl/fl}$ animals, the inventors found expression of several HOXB cluster to be at least partially dependent on DOT1L in LSK cells as it was pointed out for HOXA cluster expression before[24].

Similar to disruption of the menin-MLL complex pharmacological inhibition of DOT1L resulted in HOX down regulation, cell growth inhibition, and profound differentiation of NPM1$^{mut}$ AML blasts. These data confirm the inventor's previously build hypothesis that HOX expressing leukemias lacking an oncogenic MLL-fusion protein may also be reliant on DOT1L[24, 50] and extent this concept to the much more prevalent AML subtype with NPM1$^{mut}$.

High expression of early HOXA and HOXB cluster genes is a characteristic feature consistently found in human NPM1$^{mut}$ AML blasts and in murine models of NPM1$^{mut}$ leukemia[32, 33, 51]. The strong oncogenic transformation potential of HOX genes in general suggests that these genes are likely required for NPM1$^{mut}$ driven leukemogenesis, whereas formal proof was still lacking. Findings of the present disclosure provide strong support for this concept as exogenous overexpression of selected HOX genes rescues antiproliferative effects of both DOT1L and menin-inhibitors. The inventors further show that combinatorial inhibition of DOT1L and menin has enhanced on-target activity as reflected by more profound HOX and MEIS1 suppression. These changes result in a synergistic antiproliferative and boosted differentiation effect, suggesting that therapeutic HOX targeting ultimately releases the differentiation block of NPM1$^{mut}$ AML blasts.

Another potentially important therapeutic implication of the present disclosure is the finding that MEIS1 and FLT3 were among the most significantly suppressed genes following menin-MLL and/or DOT1L inhibition. As FLT3 was suggested to be a transcriptional target of MEIS1[52], it is likely that this suppression is conveyed via MEIS1 rather than a direct effect caused by MLL or DOT1L inhibition. Internal tandem duplications of FLT3 lead to constitutional activation of this pathway and are found in about 30% of NPM1$^{mut}$ AMLs[8]. Thus, herein proposed drug regimen of combined menin-MLL/DOT1L inhibition may particularly be attractive for patients exhibiting the adverse NPM1$^{mut}$ FLT3-ITD genotype.

Whereas data of the present disclosure provide evidence that HOX genes and MEIS1 in NPM1$^{mut}$ leukemias are regulated on a chromatin level via MLL and DOT1L, the specific role of the mutant NPM1 protein with regard to HOX and MEIS1 regulation remains elusive. However, based on the data disclosed herein, the inventors propose that the mutant NPM1 protein acts upstream of menin-MLL and DOT1L in transcriptional regulation, at least partially analogous to the functions of MLL-fusion proteins in MLL-rearranged leukemias.

The availability of menin-MLL and DOT1L inhibitors should enable relatively quick translation of our findings into clinical testing. However, future studies will determine whether the potent anti-leukemic activity can be best harnessed when introduced into current standard chemotherapy regimens, thereby overcoming possible context-specific escape mechanisms that are frequently observed in AML[53]. A proof of principle study on leukemia cell lines already demonstrated drug synergism of EPZ-5676 with standard chemotherapeutic agents in vitro[54]. Another interesting combination partner might be dactinomycin that directly inhibits transcriptional elongation by inhibition of RNA Polymerases and was reported to have activity against NPM1$^{mut}$ leukemia in an anecdotal report on a single patient[55].

In summary, the findings of the present disclosure provide insight into how HOX and MEIS1 expression is regulated on a chromatin level in NPM1$^{mut}$ AML. The inventors further identified the menin-MLL interaction and the H3K79 methyltransferase DOT1L as novel therapeutic targets for this relatively common AML subtype. Also, the inventors discovered that these two proteins control differentiation and that small molecule inhibition of each protein releases the differentiation block of NPM1$^{mut}$ leukemic blasts. Furthermore, combinatorial treatment with both compounds promotes an additive suppression of selected HOX and MEIS1 genes ultimately resulting in synergistic anti-leukemic activity. Both compounds as single agents or in combination represent novel and possibly less toxic therapeutic opportunities for patients with NPM1$^{mut}$ leukemia and might potentially improve the prognosis of patients from the adverse subsets such as concomitant FLT3-ITD, relapsed leukemia, and the difficult to treat elderly population.

Inhibitors of Interaction of MLL and Menin

Several of these inhibitors have been identified and are commercially available or at a minimum their structures publicly disclosed. Borkin yet al, Cancer cell, 27, 589-602 discloses the structure of a number of inhibitors including MI 136, MI-463 and MI 503, duplicated below. The structure of MI-0202 is also published and duplicated below in Table 1.

TABLE 1

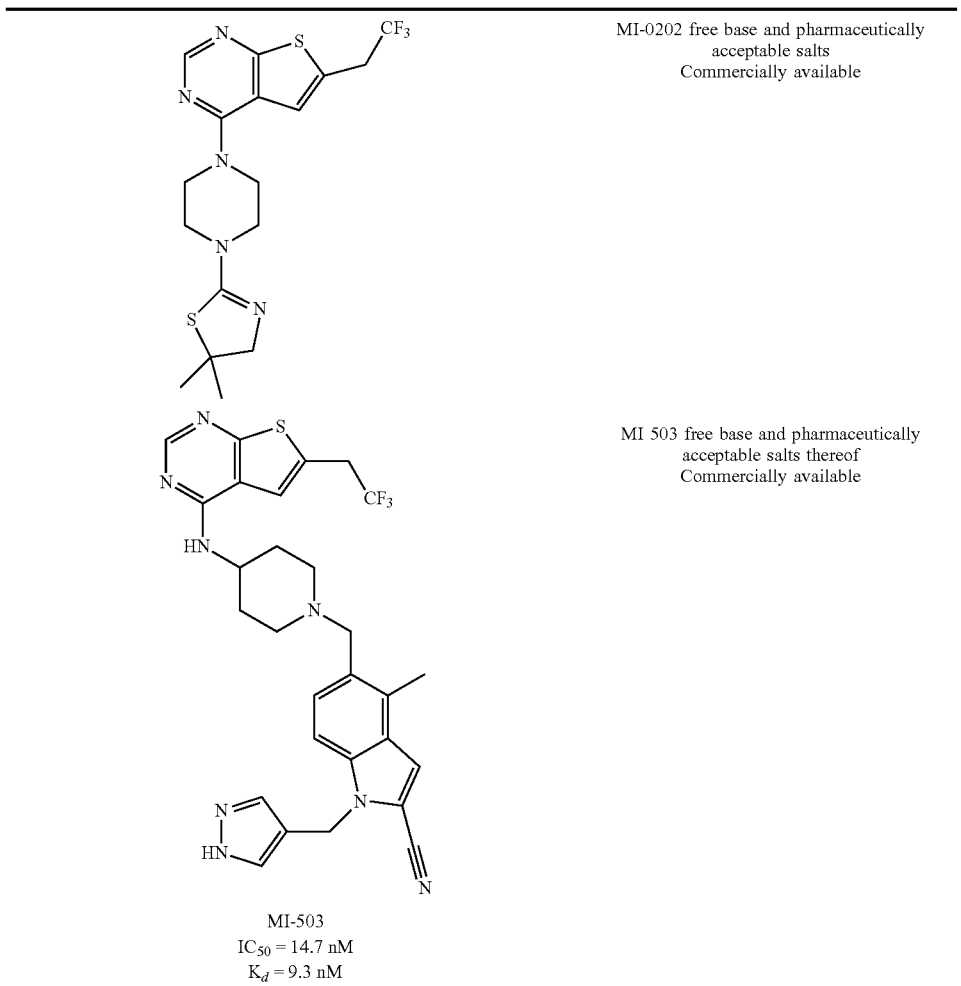

MI-0202 free base and pharmaceutically acceptable salts
Commercially available

MI 503 free base and pharmaceutically acceptable salts thereof
Commercially available MI-503
IC$_{50}$ = 14.7 nM
K$_d$ = 9.3 nM TABLE 1-continued

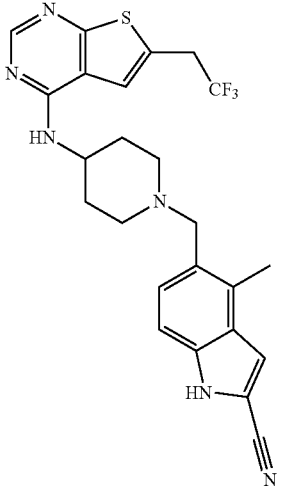

MI-463
IC$_{50}$ = 15.3 nM
K$_d$ = 9.9 nM

C  Commercially available

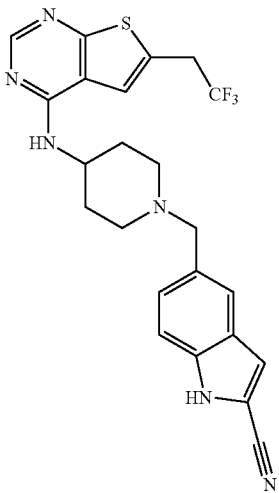

MI-136
IC$_{50}$ = 31.0 nM
K$_d$ = 23.6 nM

A  Commercially available

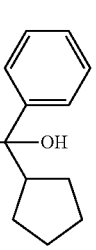

ML 227 Structure and synthesis published in Inhibitors of the Menin-Mixed Lineage Leukemia (MLL) Interaction by Jason Manka et al. in Probe Reports from the NIH Molecular Libraries Program Updated Feb. 28, 2013, http://www.ncbi.nlm.nih.gov/books/NBK133428/ last visited Jan. 26, 2016.

Additional MLL-menin interaction inhibitors are disclosed in:

High-Affinity Small-Molecule Inhibitors of the Menin-Mixed Lineage Leukemia (MLL) Interaction Closely Mimic a Natural Protein-Protein Interaction, Shihan He, et al, dx.doi.org/10.1021/jm401868d|J. Med. Chem. February 27; 57(4):1543-56. Borkin, D et al, Cancer Cell, 27, 589-602, 2015.

U.S. Pat. No. 8,993,552 (371 application of WO 2011/029054) and U.S. Pat. No. 8,242,078 (371 application of WO 2008/070303) disclosing such inhibitors are incorporated by reference in their entirety for all purposes. Additional examples can be found in the Table 2 below:

TABLE 2

Structures and IC$_{50}$ Values for Hydroxymethylpiperidine Inhibitors of the Menin-MLL Interaction.

| Compound | R$_2$ | —X | R$_3$ | R$_4$ | IC$_{50}$ (μM) |
|---|---|---|---|---|---|
| 1 (MIV-1) | phenyl | —OH | —CN | —OH | 12.8 ± 1.6 |
| 2 (MIV-2) | phenyl | —OH | —CN | —H | 10.8 ± 0.2 |
| 3 | phenyl | —H | —CN | —H | 205 ± 63 |
| 4 | phenyl | —OH | —H | —H | >250 |
| 5 (MIV-nc) | —H | —OH | —CN | —H | 234 ± 22 |
| 6 | —CH$_3$ | —OH | —CN | —H | 295 ± 50 |
| 7 | cyclobutyl-like | —OH | —CN | —H | 15.3 ± 3.8 |
| 8 | cyclopropyl | —OH | —CN | —H | 11.2 ± 3.9 |
| 9 | isopropyl | —OH | —CN | —H | 4.1 ± 0.6 |
| 10 | cyclobutyl | —OH | —CN | —H | 4.0 ± 1.4 |
| 11 MIV-3 | cyclopentyl | —OH | —CN | —H | 0.39 ± 0.04 |
| 12 | cyclohexyl | —OH | —CN | —H | 1.7 ± 0.6 |

The foregoing compounds in Table 2 can be synthesized as described in J. Med. Chem. February 27; 57(4):1543-56 including the supplement thereof.

Effective amounts of the MLL-menin interaction inhibitors are within the following ranges for their IC50: from about 100 nM to about 10 μM or from about 250 nM to about 5 μM or from about 500 nM to about 1 μM. Smaller amounts may be effective if these inhibitors are administered in combination with a DOT1L inhibitor.

As used herein the phrase "in combination" encompasses both substantially simultaneous administration as well as sequential administration of one or more members of each class of inhibitor disclosed herein. Sequential administrations may be within the same day, or administration may be spaced apart by a time interval of at least a day or a week or two weeks or three weeks or a month or even longer.

The two inhibitors may be administered sequentially in any order. For example, the MLL-menin interaction inhibitor may be administered first followed by the DOT1L inhibitor or vice versa.

Each inhibitor may be formulated into a pharmaceutical formulation, such as those disclosed for DOT1L inhibitors in U.S. Pat. No. 10,407,732 (371 application of WO 2015/017863), incorporated by reference in its entirety.

DOT1L Inhibitors

Several such inhibitors have been disclosed in WO2015/017863 along with ranges of effective amounts in terms of IC 50 of inhibition being within a range from about 100 nM to about 10 μM or from about 250 nM to about 5 μM or from about 500 nM to about 1 μM. Examples are the following: EPZ005676, EPZ004777, SGC-0946, SYC-522, SYC-534, and SYC-687. These and additional DOT1L inhibitors are disclosed in the following publications: US 2015/0342979 (371 application of WO 2014/100662); US 2015/0284422A1 (371 application of WO 2014/026198); U.S. Pat. No. 9,597,348 (371 application of WO 2014/039839); U.S. Pat. No. 8,580,762 (371 application of WO 2012/075381); U.S. Pat. No. 9,394,310 (371 application of WO 2012/075492); U.S. Pat. No. 9,029,343 (371 application of WO 2012/082436); U.S. Pat. No. 9,145,438 (371 application of WO 2012/075500); U.S. Pat. No. 8,722,877; and US 20140100184, each being incorporated by reference herein in its entirety; and as described in WO 2016/025649. Examples are as follows:

DOT1L inhibitors that may be suitably employed in the presently disclosed methods for inhibiting the proliferation and/or survival of cell and for treatment of leukemia patients include the 7-deazapurine compounds as described in WO 2012/075500 and WO/2012/082436 as represented by Formula I:

Formula I

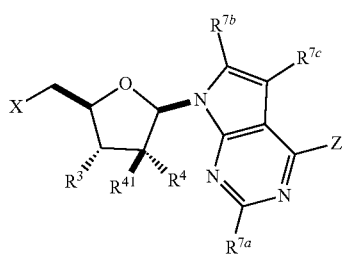

DOT1L inhibitors that may be suitably employed in the presently disclosed methods for inhibiting the proliferation and/or survival of cell and for treatment of leukemia patients include carbocycle-substituted purine and 7-deazapurine compounds as described in WO 2012/075492 as represented by Formula II:

Formula II

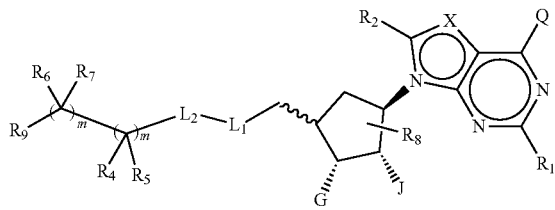

DOT1L inhibitors that may be suitably employed in the presently disclosed methods for inhibiting the proliferation and/or survival of cell and for treatment of leukemia patients include purine and 7-deazapurine compounds as described in US 2012/0142625 and WO 2012/075381 as represented by Formula III:

Formula III

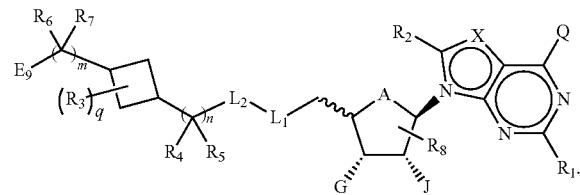

Compounds that are encompassed within the range of compounds defined by Formulas I, II, and III, and methodologies for the synthesis of those compounds, are presented in U.S. Patent Publication No. 2012/0142625 and PCT Patent Publication Nos. WO 2012/075381; WO 2012/075492; WO 2012/075500; and WO 2012/082436. Two exemplary such compounds are EPZ004777 and EPZ005676, which are presented in the following section along with a description of methodologies for synthesizing those compounds from readily available starting materials (e.g., Sigma-Aldrich, St. Louis, Mo.).

EPZ004777

The small molecule DOT1L inhibitor EPZ004777 is an s-adenosyl methionine mimetic is highly specific for DOT1L as compared to other methyl transferases. Daigle et al., *Cancer Cell* 20(1):53-65 (2011) and Yu et al., *Nat. Commun.* 3:1288 (2013). EPZ004777 binds within the S-(5'-adenosyl)-1-methionine (SAM) binding site in the catalytic domain of human DOT1L.

Compositions and Methods of Administration of DOT1L Inhibitor and of MLL-Menin-MLL Interaction Inhibitors An inhibitor from either class will generally be administered parenterally in a physiologically acceptable vehicle as disclosed for DOT1L inhibitors in WO2015/017863.

"Parenteral administration" refers to modes of administration other than enteral and topical administration, usually by injection, and include, without limitation, intravenous, intramuscular, intraarterial, 5 intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be by oral route.

Various compositions containing one or both inhibitors are contemplated as disclosed in WO2015/017863 for DOT1L inhibitors. Excipients, carriers and diluents are as disclosed in WO2015/017863 for DOT1L inhibitors. Units dosage form amounts are also as disclosed in WO2015/017863 for DOT1L inhibitors.

Compositions and Formulations Comprising Inhibitors of Menin MLL Interaction or DOT1L Inhibitors or Both The present disclosure provides compositions, including therapeutic compositions comprising one or more DOT1L inhibitor(s) and/or one or more inhibitor(s), for the treatment of a leukemia, such as ALL or AML. One or more DOT1L inhibitor(s) and/or one or more menin-MLL interaction inhibitor(s) can be administered to a human patient individually as monotherapy or combinedly in individual formulations. In such formulations the active ingredient or ingredients are mixed with suitable carriers or excipient(s) at doses to treat or ameliorate leukemia such as ALL or AML as described herein. Mixtures of these inhibitors can also be administered to the patient as a simple mixture or in suitably formulated pharmaceutical compositions.

Compositions within the scope of this disclosure include compositions wherein the therapeutic agent is provided in an amount effective to inhibit the proliferation of a leukemia cell in a patient. Determination of optimal ranges of effective amounts of each component and duration of administration is within the skill of the art. The effective dose and/or duration is a function of a number of factors, including the specific inhibitor and its half-life in the body of the patient, the presence of a prodrug, the incidence and severity of side effects, the age, weight and physical condition of the patient and the clinical status of the latter. The dosage administered and duration of the administration may also be dependent on the kind of concurrent treatment, if any, frequency of treatment, and the nature of the effect desired. Cycles of administration followed by periods of no treatment are also contemplated.

Compositions comprising one or more inhibitors according to the present disclosure may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be orally.

Examples of parenteral administration include intravenous administration via an intravenous push or bolus. Alternatively, compositions according to the present disclosure may be administered via an intravenous infusion.

Suitable dosages for intravenous infusion of a composition comprising an inhibitor of menin-MLL interaction alone or in combination with a DOT1L inhibitor include a dosage of at least about 2 mg inhibitor/m2/day or at least about 10 mg inhibitor/m2/day or at least about 20 mg inhibitor/m2/day or at least bout 50 mg inhibitor/m2/day or at least about 100 mg inhibitor/m2/day or at least about 200 mg inhibitor/m2/day or at least about 500 mg inhibitor/m2/day or maximum tolerated dose if lower.

Compositions comprising a DOT1L inhibitor and/or a menin-MLL interaction inhibitor generally include a therapeutically effective amount of a compound, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients for solid and/or liquid formulations may be selected by those skilled in the art as appropriate for a particular formulation among for example starch, glucose, lactose, sucrose, gelatin, malt, rice, flour, chalk, silica gel, sodium stearate, glycerol monostearate, talc, sodium chloride, dried skimmed milk, glycerol, propylene glycol, water, ethanol and the like. The composition, if desired, can also contain minor amounts of wetting or emulsifying agents, or pH buffering agents.

These compositions can take the form of solutions, suspensions, emulsions, tablets, pills, capsules, powders, sustained-release formulations and the like. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like. Such compositions will contain a therapeutically effective amount of at least one inhibitor, preferably in purified form, together with a suitable amount of carrier so as to provide the form for proper administration to the patient. The formulation should suit the mode of administration. Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients are supplied either separately or mixed together in unit dosage form, for example, as a dry lyophilized powder or water free concentrate in a 5 hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The inhibitors disclosed herein can be formulated as free base (or acid) or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Many of the inhibitors of the present disclosure may be provided as salts with pharmaceutically compatible counterions (i.e., pharmaceutically acceptable salts).

A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a subject. Pharmaceutically acceptable salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes such salts.

Use of the MLL-Menin Inhibitors in Humans

It is anticipated that the MLL-Menin interaction inhibitors will be likely used every day for a period of time ranging from one week or two weeks or three weeks up to about 3 months or 6 months or 8 months or 1 year or 2 years. The inhibitor can be administered daily throughout this period or can be given for a period of days followed by a period of no treatment and then followed by resumption of treatment. The exact administration protocol can be determined by those skilled in the art.

The amounts administered have been discussed above.

If a DOT1L inhibitor is used in addition, a similar protocol is anticipated, subject to any adjustment to dosage of one or the other inhibitor as described above and subject to allowances in administration protocol for simultaneous or sequential administration of each inhibitor as taught above and as appreciated by those skilled in the art.

EXAMPLES

The following Examples further illustrate the findings of the present disclosure.

Example 1

CRISPR-Cas9 Mutagenesis Demonstrates a Requirement for MLL1 and the Menin Binding in NPM1$^{mut}$ Leukemia Since MLL1 has been shown to regulate critical gene expression programs, including HOX gene expression in normal hematopoiesis and MLL-rearranged AML, the inventors hypothesized that it might also regulate HOX gene expression in other settings. As an initial assessment, the inventors used an approach recently developed by Shi and co-workers that uses genome editing across exons encoding specific protein domains to determine the functional relevance of a given domain and the suitability for drug development[31]. To assess potential dependencies of NPM1$^{mut}$ AML on specific protein domains of MLL and its most similar family member MLL2, a negative selection CRISPR-Cas9 screen interrogating multiple domains of both proteins was designed. The inventors generated a tetracycline-inducible Cas9-expressing OCI-AML3 cell line (OCI-AML3-pCW-Cas9, FIG. 1A and FIG. 1). After transduction with 2-4 GFP$^+$ sgRNAs interrogating each domain, Cas9 was induced and GFP$^+$/GFP$^-$-ratio assessed over a period of 15 days. Cells expressing sgRNAs targeting exon 1 that encodes the menin-binding domain of MLL were rapidly outcompeted by their GFP$^-$ counterparts (FIG. 1C and FIG. 1E; fold change of GFP+ d0/d15 up to 100). Similar results were obtained for one of two sgRNAs targeting the first exon of RPA3, a gene required for DNA replication that is used as a positive control, while there was no difference in GFP expression over time in two independently transduced empty vector control guides (FIG. 1C). Interestingly, sgRNAs targeting exons that encode the CXXC domain of MLL, also known to be involved in chromatin binding and for MLL-fusion leukemia, were the selected against in our screen (FIG. 1C and FIG. 1F). Of interest, no significant phenotype was observed for sgRNAs targeting the C-terminal SET domain of MLL (FIG. 1C). These findings were validated by performing a second screen using another independently engineered OCI-AML3-pCW-Cas9 clone (OCI-AML3-pCW-Cas9-C8, FIG. 1D), where similar results were obtained with sgRNAs targeting the menin binding domain being again the top hit. The inventors found no significant negative selection for any guides that interrogated the MLL2 protein domains (FIG. 1D). These data indicate that the menin-binding domain of MLL1 but not MLL2 is required for NPM1$^{mut}$ AML.

Example 2

Pharmacological Disruption of the Menin-MLL Interaction Suppresses HOX, MEIS1 and FLT3 Expression and Induces NPM1$^{mut}$ AML Differentiation The genetic data presented above indicate that the menin-MLL interaction might be a therapeutic target in NPM1$^{mut}$ AML. The inventors next assessed whether recently developed small molecule inhibitors of the menin-MLL interaction might influence proliferation and gene expression in NPM1$^{mut}$ AML cells. First, the effects of an inhibitor of the MLL-Menin interaction, MI-2-2 on the human NPM1$^{mut}$ AML cell line OCI-AML3 were assessed[21]. The inventors observed a profound dose-dependent reduction in cell proliferation that was even more pronounced than in the MLL-AF9-rearranged MOLM-13 cells that served as a positive control (FIG. 2A). The HL-60 AML cells lacking an NPM1$^{mut}$ or MLL-rearrangement showed only a mild cell growth inhibitory effect at higher doses (FIG. 2A). Next, gene expression was assessed in the NPM1$^{mut}$ AML cells where a significant down regulation of HOXA, HOXB cluster and MEIS1 gene expression upon 4 days of treatment with MI-2-2 (FIG. 2B) was observed. Of these, MEIS1 appears to be the most profoundly suppressed gene. This finding prompted the inventors to explore a possible effect of menin-MLL inhibition on FLT3 expression, as FLT3 is a reported downstream target of MEIS1 (Argiropoulos et al. Genes Dev. 2007 Nov. 15; 21(22):2845-9). In fact, FLT3 transcript levels were also substantially and highly significantly suppressed upon menin-MLL inhibition (FIG. 2B).

Next, the inventors sought to validate the above findings in two independent murine conditional knock-in models of NPM1$^{mut}$ leukemia. One of the leukemias is engineered to possess both an NPM1 mutation and a Flt3-ITD (Npm1$^{CA/+}$Flt3$^{ITD/+}$), whereas the other model possesses an NPM mutation and secondary mutations that were induced through use of a Sleeping Beauty transposon system (Npm1$^{CA/+}$Rosa$^{SB/+}$).[32, 33] Additionally, MI-503, a novel menin-MLL inhibitor was recently described[22] that was synthesized by re-engineering the molecular scaffold of MI-2-2 resulting in enhanced drug-like properties. Experiments on the murine cells were therefore performed using MI-503. To compare the two compounds and to define equivalent growth inhibitory concentrations, dose response curves for both inhibitors were generated, confirming the higher potency of MI-503 over MI-2-2 in human and murine NPM1$^{mut}$ leukemia cells (FIG. 2A).

For drug testing experiments, leukemic blasts were harvested from moribund primarily transplanted mice and cultured in vitro. MI-503 treatment was performed in colony forming assays and liquid culture proliferation assays as Npm1$^{CA/+}$Rosa$^{SB/+}$ cells grew in methylcellulose and Npm1$^{CA/+}$Flt3$^{ITD/+}$ cells grew in liquid culture medium. Similar to the human cells, we observed a profound inhibitory effect on colony forming potential and cell growth in both NPM1$^{mut}$ as well as Mll-Af9 leukemia cells in response to menin-MLL inhibition, while Hoxa9-Meis1 transformed cells were unaffected (FIG. 2C).

Analogous to what has been observed in the OCI-AML3 cells, the inventors observed significant down regulation of Hoxa and Hoxb cluster genes as well as Meis1 after four days of MI-503 treatment. Whereas baseline expression levels of the early Hoxb cluster genes differed among the murine leukemias—with the Npm1$^{CA/+}$Flt3$^{ITD/+}$ cells for example lacking expression of Hoxb2—Meis1 was again most profoundly suppressed in both leukemias and accompanied by substantial down regulation of global Flt3 transcript levels (FIG. 2D).

Whereas induction of apoptosis was moderate following menin-MLL inhibition, the inventors noted a strong differentiation inducing effect in all three NPM1$^{mut}$ leukemia models as reflected by morphological changes consistent with monocytic and granulocytic features (FIG. 2F) as well as a profound increase in CD11b expression as determined by flow cytometry (FIG. 2F; vehicle vs. MI-2-2: 1.3% vs. 72% on day seven of treatment).

These data indicate that pharmacological menin-MLL inhibition causes down regulation of HOX genes, MEIS1 and FLT3 followed by differentiation and cell growth inhibition.

Example 3

Retrovirally Induced Overexpression of HOX Genes Rescues the Menin-MLL Inhibitor Antiproliferative Effect As changes in HOX and MEIS1 gene expression (day 4; FIG. 2B and FIG. 2D) preceded cell differentiation and growth inhibitory effects following menin-MLL inhibition, it was hypothesized that HOX and MEIS1 gene expression controls cell proliferation and differentiation in NPM1$^{mut}$ AML cells.

Thus, the inventors investigated the effect of ectopic expression of Meis1, Hoxb4, and Hoxa9-Meis1 in the Npm1$^{CA/+}$Flt3$^{ITD/+}$ murine leukemia cells. In all three cases overexpression of these genes was observed to rescue the Npm1$^{CA/+}$Flt3$^{ITD/+}$ cells from the menin-MLL antiproliferative effect as indicated by a shift of the dose response curves towards higher concentrations and increased IC$_{50}$ values (FIG. 2D). Thus, pharmacological menin-MLL inhibition inhibits cell proliferation in NPM1$^{mut}$ AML cells most likely via alteration of Hox and Meis1 expression.

Example 4

Menin-MLL Inhibition Reduces Leukemia Burden In Vivo and Improves Survival of NPM1$^{mut}$ Leukemic Mice The inventors next investigated the therapeutic effects of menin-MLL inhibition in vivo using a disseminated human OCI-AML3 xenotransplantation model. OCI-AML3 cells were transplanted into NSG mice via tail vein injection and MI-503 treatment was initiated seven days later. Animals were sacrificed after seven (n=2 per group) and 12 days (n=3 per group) of MI-503 treatment (50 mg/kg bid IP). Leukemia burden, as defined by the percentage of bone marrow cells expressing human CD45, was significantly reduced within the treated animal group compared to vehicle controls (FIG. 2G). Furthermore, analysis of HOXB4, MEIS1 and FLT3 in sorted human CD45 positive cells harvested from these animals exhibited a dramatic decrease of expression levels in the MI-503 treated versus vehicle control animals (FIG. 2H).

Example 5

Figure 3:
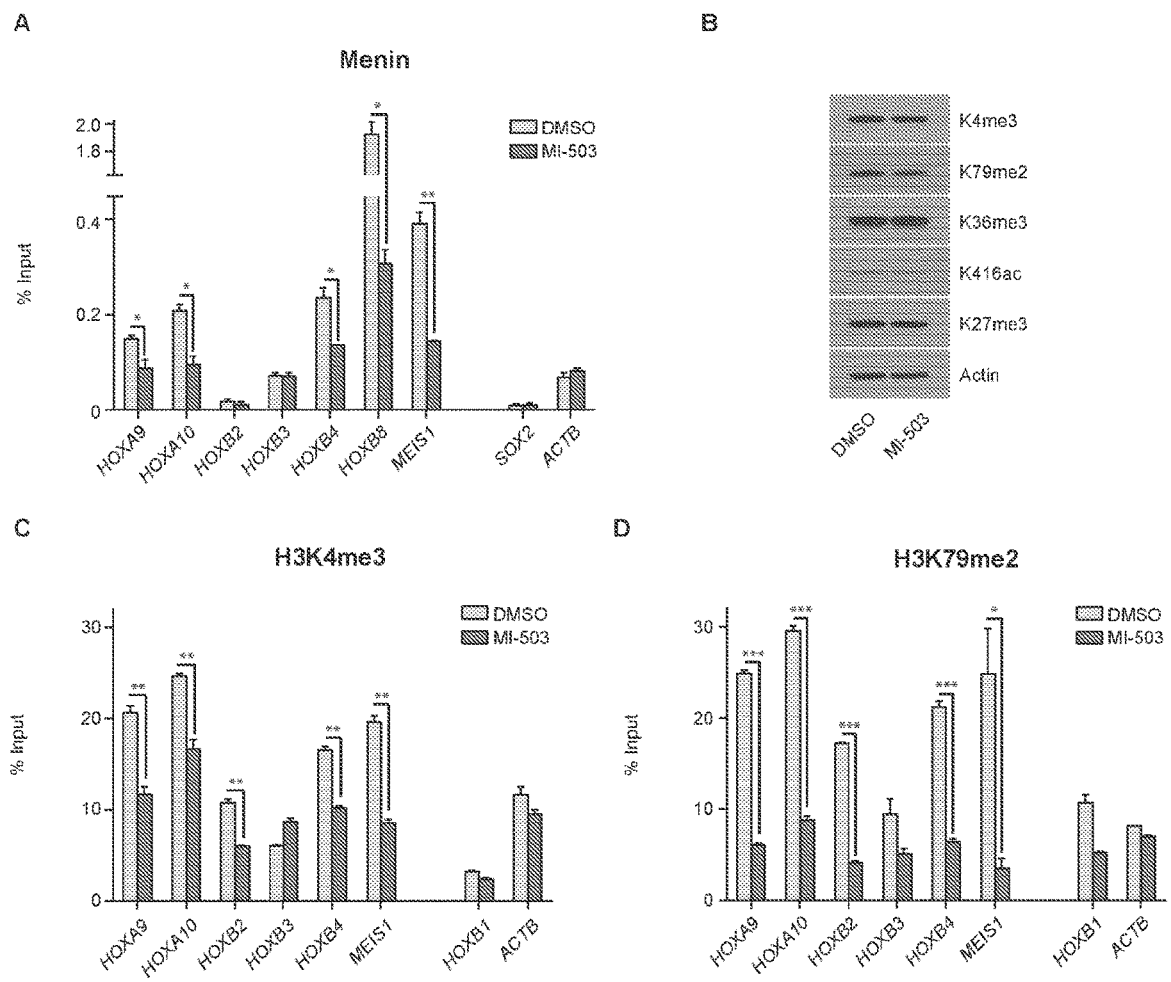
FIGS. 3A-D are graphs and a blot showing that menin-MLL inhibition depletes menin, H3K4me3, and H3K79me2 at HOX and MEIS1 gene loci in OCI-AML3 cells.

MI-503 Treatment Depletes Menin from HOX and MEIS1 Loci in NPM1$^{mut}$ Leukemias Menin associates with MLL1 at HOXA and MEIS1 promoters[19] and pharmacological interruption of the menin-MLL interaction diminishes menin occupancy at the HOXA locus in MLL-rearranged leukemias[34]. The abundance of menin at HOXA, HOXB and MEIS1 loci was assessed in NPM1$^{mut}$ leukemias before and after pharmacological menin-MLL inhibition. Using Chromatin Immunoprecipitation (ChIP) of menin followed by quantitative PCR in the human NPM1$^{mut}$ leukemia cell line OCI-AML3, the inventors demonstrated presence of menin at expressed HOXA, HOXB and MEIS1 gene loci (FIG. 3A). MI-503 treatment depleted menin from most of these loci and was most significantly reduced at the MEIS1 locus thereby correlating with gene expression levels (FIG. 3A and FIG. 2B). Whereas global assessment of several chromatin marks did not reveal any changes upon menin-MLL inhibition (FIG. 2B) the inventors observed a locus specific decrease of H3K4 trimethylation marks at HOX and MEIS1 loci (FIG. 2C), thus demonstrating the expected changes is histone methylation due to Menin inhibition. Somewhat unexpectedly, a dramatic reduction of H3K79 dimethylation (H3K79me2) was also observed at those loci as it has been observed in MLL-rearranged leukemias (FIG. 2D). These data are consistent with decreased binding of the menin-MLL complex to HOX and MEIS loci following menin-MLL inhibition and also point to the H3K79 methyltransferase DOT1L as having a potential role in HOX gene regulation in NPM1$^{mut}$ leukemia cells.

Example 6

DOT1L is Involved in HOXA and HOXB Cluster Regulation During Normal Hematopoiesis and in NPM1$^{mut}$ Leukemia The data described above suggest wt-MLL1 to be important for HOX gene control in NPM1$^{mut}$ AML, and also implicate DOT1L in HOX gene regulation in this disease. Recent studies of benign murine hematopoiesis demonstrated that DOT1L is another chromatin regulator critical for HOXA cluster regulation in early hematopoietic progenitors, whereas its role in HOXB cluster control is not well defined. To explore whether DOT1L might be involved in the control of HOXB cluster genes expression, we reanalyzed gene expression data from Dot1l$^{fl/fl}$ Mx1-Cre transgenic mice after polyinosinic-polycytidylic acid (pIpC) induced excision compared to their normal counterparts. In fact, the inventors found the early HOXB cluster genes HOXB2 and HOXB4 significantly down regulated after homozygous deletion of DOT1L (FIG. 4a), while there was also a trend for HOXB3 that did not reach statistical significance. In addition, there was an association between high expression levels of early HOXB cluster genes and higher states of H3K79 methylation (H3K79me2 and me3) in normal murine Lin−, Sca1+, c-Kit+ (LSK) cells (FIG. 4b) mimicking the H3K79 profile across the expressed HOXA cluster genes in these cells. These findings extend the concept of DOT1L being critical for HOXA cluster regulation during normal hematopoiesis to the HOXB cluster, which together represents also the dominant expression pattern found in NPM1$^{mut}$ leukemias.

Figure 4:
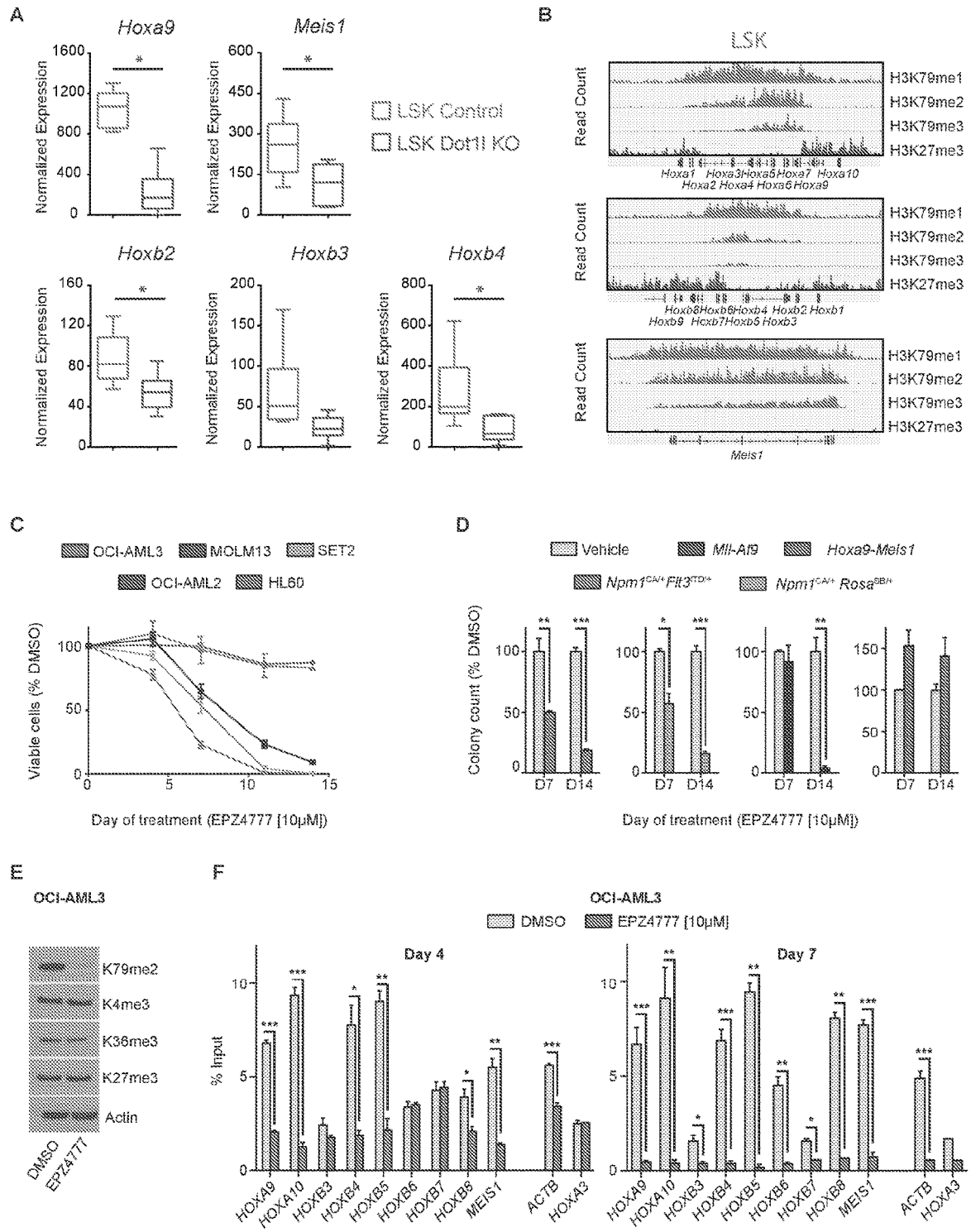
FIGS. 4A-F are graphs and blots showing that DOT1L is required for HOXB cluster expression in early hematopoietic progenitors and a therapeutic target in NPM1$^{mut}$ leukemia.

Based on these findings, the inventors assessed the effect of EPZ4777, a small molecule DOT1L inhibitor in NPM1$^{mut}$ leukemias. DOT1L inhibition led to a profound reduction in cell proliferation and colony forming potential in the human and the murine leukemia cells. Similar results were obtained for MLL-fusion leukemias whereas leukemias lacking an NPM1 mutation or MLL-fusion such as the HL-60 cells and Hoxa9-Meis1 in vitro transformed cells were unaffected (FIG. 4C and FIG. 4D). The antiproliferative effects of DOT1L inhibition were preceded by global and HOXA and HOXB loci specific reduction in H3K79me2 marks as determined by immunoblotting and ChIP-PCR, whereas global levels of other histone marks associated with transcriptional activation (H3K4me3, H3K36me3) and transcriptional repression (H3K27me2) were unchanged (FIG. 4E). As hypothesized, DOT1L inhibition resulted in significant repression of HOX genes in both models (FIG. 5A, left panel and FIG. 5), while the specific pattern of affected genes differed slightly among the different models. As murine leukemias exhibited significant suppression of HOXA and HOXB cluster genes, the human OCI-AML3 cells showed most significant down regulation of MEIS1 and the HOXB cluster only as assessed by RNA-sequencing (FIG. 5A). Of note, MEIS1 was the most consistently and profoundly down regulated gene across all NPM1$^{mut}$ models and was accompanied by dramatic suppression of FLT3 expression (FIGS. 5A and B). As global changes in H3K79 methylation marks might be associated with transcriptional up- or down regulation that in turn can also lead to profound normalization bias of RNAseq data, the findings were validated using ERCC-control sequences that were spiked-into the specimens as suggested by Young and others[35]. There was no difference of HOX or global transcription levels between the different normalization methods, indicating that global reduction of H3K79me2 is not associated with global transcriptional down regulation but with suppression of a smaller subset dominated by HOX genes in these cells. As demonstrated for menin-MLL inhibition, it was found that retroviral overexpression of Hoxb4, Meis1, or Hoxa9-Meis1 abolished sensitivity of Npm1$^{CA/+}$Flt3$^{ITD/+}$ cells to DOT1L inhibition (FIG. 2C).

Besides suppression of HOX genes and MEIS1, Gene Set Enrichment Analysis (GSEA) of RNAseq data on the OCI-AML3 cells identified a dominant set of genes up regulated upon DOT1L inhibition that was significantly enriched for genes usually silenced in HSCs and mainly containing genes associated with myelo-monocytic differentiation (FIG. 5A). Accordingly, profound induction of differentiation was observed in human and murine NPM1$^{mut}$ leukemia cells following DOT1L inhibition. (FIG. 5C and FIG. 5D). These data are therefore consistent with DOT1L participating in HOX gene regulation and differentiation control of NPM1$^{mut}$ leukemia cells.

Example 7

DMT3A Mutations do not Account for Sensitivity of NPM1 Mutant AML

Besides the NPM1 mutation OCI-AML3 cells also carry a DNMT3A mutation (R882C), which is associated with aberrant HOX expression in AML. To explore whether DNMT3A mutation status is associated with sensitivity to DOT1L inhibition, the inventors included two additional cell lines with DNMT3A mutations in the study. The JAK2 mutated SET2 cells were recently reported to carry the most common DNMT3A mutation found in AML patients (R882H), whereas OCI-AML2 cells carry a DNMT3A mutation that has so far been reported only in a single patient with myelodysplastic syndrome (R635W)[36]. Whereas the SET2 cells did not show any sign of sensitivity to DOT1L-inhibition, the OCI-AML2 cells were substantially sensitive to DOT1L inhibition (FIG. 4C).

To understand these conflicting findings, the inventors searched for the presence of other genetic factors potentially mediating sensitivity to EPZ4777 in the OCI-AML2 cells. Surprisingly, RNA sequencing revealed the presence of an MLL-AF6 fusion transcript with breakpoints that aligned to the common breakpoint cluster region typically affected in MLL-AF6 rearranged leukemias. Breakpoint spanning RT-PCR confirmed the presence of the fusion transcript. Whereas conventional cytogenetic analysis revealed two normal 11q23 loci, a MLL split signal was detected within the derivative chromosome 1q. These findings are consistent with the presence of a functionally relevant cryptic MLL-AF6 fusion inserted into the derivative chromosome1. Also, the inventors observed high-level expression of HOXA but not HOXB cluster genes that were profoundly down regulated upon DOT1L inhibition.

Together, these data support a previous study (U.S. Pat. No. 10,407,732 (371 application of WO 2015/017863) which is incorporated by reference) reporting that DOT1L controls HOXA cluster expression also in MLL-fusion leukemia with no apparent DOT1L recruiting activity (such as MLL-AF6). However, whether DNMT3A mutations are associated with sensitivity to DOT1L inhibition remains to be determined.

Example 8

Pharmacological DOT1L Inhibition Diminishes Leukemia Initiating Potential

As HOXgene expression is associated with self-renewal properties, the inventors next determined whether pharmacological DOT1L inhibition inhibits NPM1$^{mut}$ leukemia initiation in mice. Murine Npm1$^{CA/+}$Flt3$^{ITD/+}$ leukemia cells were treated ex vivo with EPZ4777 or drug vehicle for 10 days and equal numbers of viable cells were transplanted into sublethally irradiated recipient animals. A significant survival advantage was observed for the animals transplanted with the treated cells compared to vehicle control in both NPM1$^{mut}$ leukemia models (FIG. 5F). Whereas animals transplanted with the EPZ4777-treated Npm1$^{CA/+}$Flt3$^{ITD/+}$ leukemia cells exhibited significantly lower WBC counts at time of disease onset within the control group, all mice eventually developed full blown leukemia (FIG. 5E and FIG. 5F). Similar results were obtained for the Npm1$^{CA/+}$FLt3$^{ITD/+}$ cells but with longer disease onset within the treated group. These findings demonstrate the ability of pharmacological DOT1L inhibition to suppress leukemia initiating potential in vivo.

Example 9

Figure 6:
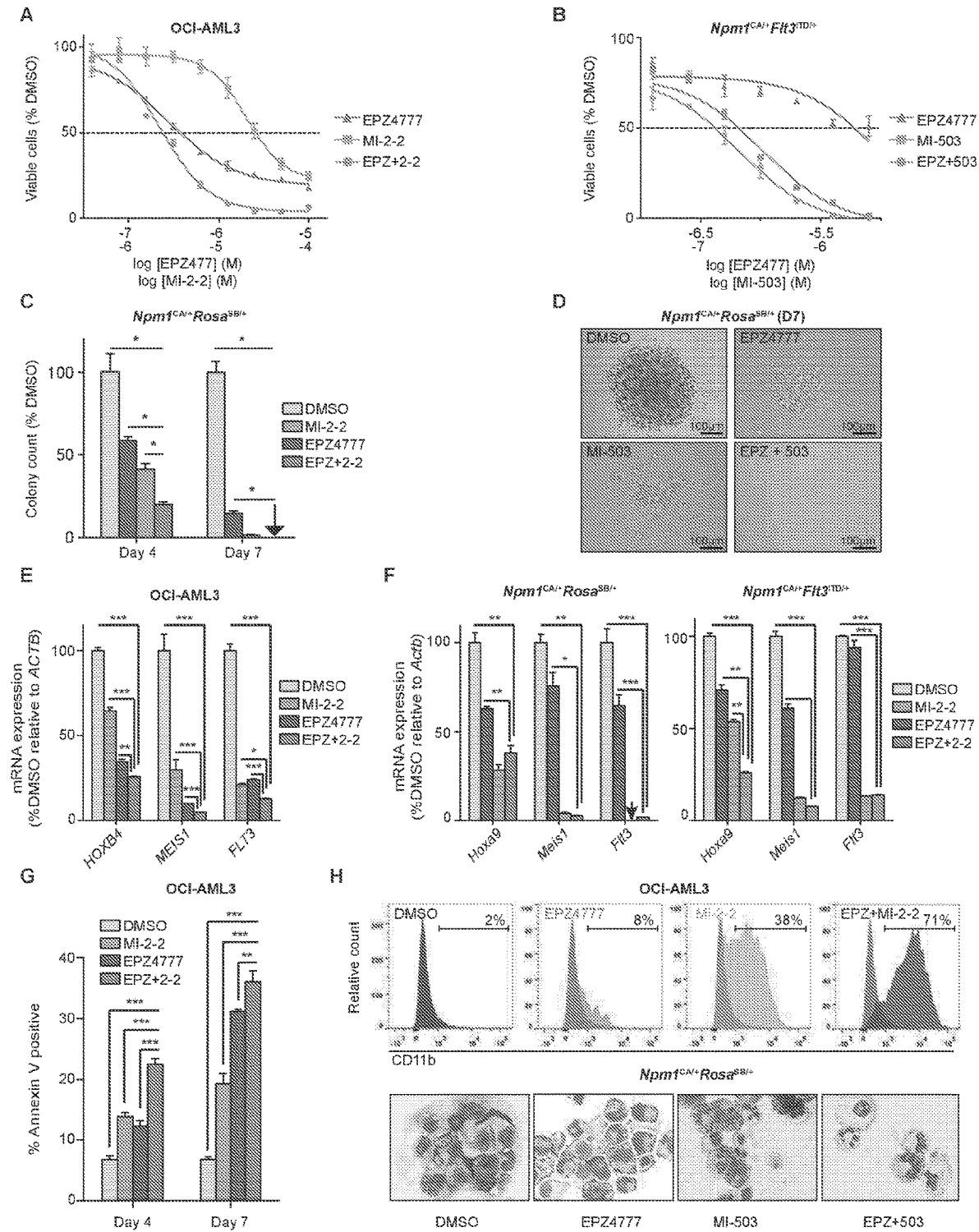
FIGS. 6A-H are graphs and images showing effects of combinatorial menin-MLL and DOT1L inhibition in murine and NPM1mut leukemia cells.

Combination of Menin-MLL and DOT1L Inhibition Synergistically Inhibits Proliferation, Suppresses HOX MEIS1, and FLT3 Expression, and Induces Differentiation in NPM1$^{mut}$ Leukemia The data presented above are consistent with the menin-MLL interaction and DOT1L being both therapeutic targets that control HOXA and HOXB cluster regulation in NPM1$^{mut}$ AML. Next, the therapeutic potential of combinatorial menin- and DOT1L inhibition in these leukemias was assessed. Simultaneous menin- and DOT1L inhibition in the OCI-AML3 cells resulted in a profound shift of the dose response curve toward lower doses compared to each of the compounds alone (FIG. 6A). Drug combination analysis using the Chou-Talalay model revealed a clear synergistic anti-proliferative effect. Drug synergism was also observed in proliferation assays of the Npm1$^{CA/+}$Flt3$^{ITD/+}$ cells (FIG. 6B) and combinatorial drug treatment resulted in significantly higher suppression of colony forming potential in Npm1$^{CA/+}$Rosa$^{SB/+}$ cells (FIGS. 6C and D). These results are also shown in FIG. 9, which provides numeric data reflecting the dose and relative growth inhibition, (i.e. effect) for the single and combination treatments for Npm1$^{CA/+}$Flt3$^{ITD/+}$ cells at day 11, illustrating synergy for the combination treatments.

These changes were preceded by significantly enhanced down regulation of selected genes with drug treatment combination (menin-MLL and DOT1L inhibition). Whereas suppression levels of specific HOXA and HOXB cluster genes differed among the different NPM1$^{mut}$ leukemia models, MEIS1 and FLT3 were consistently suppressed (FIG. 6E and FIG. 6F). Consistent with these findings, cells treated with the combination regimen exhibited significantly less RNA-Polymerase II binding to the MEIS1 promoter and gene body region than single treated cells as assessed using ChIP-PCR. These findings are therefore consistent with an enhanced inhibitory effect of MEIS1 transcription.

While the inventors also observed a significant increase in apoptosis in the cells treated with both compounds (FIG. 6G), effects on differentiation were most pronounced in all NPM1$^{mut}$ AML models and occurred earlier compared to single drug treatment (FIG. 6H).

Example 10

Combination of Menin-MLL and DOT1L Inhibition Synergistically Abolishes Leukemia Initiating Potential In Vivo Since the in vitro data showed a synergistic drug effect for simultaneous menin- and DOT1L inhibition in NPM1$^{mut}$ leukemias, the inventors examined the effect of combinatorial drug treatment on leukemia initiating potential in vivo. Equal numbers of viable cells treated with drug vehicle, EPZ4777, MI-2-2, or the combination were transplanted into sublethally irradiated recipient and assessed for engraftment. As shown in FIG. 7A, % engraftment was lower when animals were treated with both EPZ4777 and MI-2-2. These results are also shown in FIG. 10, which provides numeric data reflecting the dose and relative growth inhibition, (i.e.

effect) for the single and combination treatments, illustrating synergy for the combination treatments.

Example 11

Combination of Menin-MLL and DOT1L Inhibition Kills Primary AML Cells In Vitro In order to assess effects of drug treatment of NPM1$^{mut}$ primary AML samples, the inventors used a modified, previously published human co-culture model described in the material and methods section to maintain and/or expand human AML cells for 10 days and assess for drug sensitivity. Whereas 1 of 5 cases was not maintainable in culture and cell death occurred within 48 hours after thawing, the remaining 4 samples were treated for 10 days and viable cell numbers of human CD45+ cells were assessed in order to control for potential contamination with adherently growing stromal cells. While all cases exhibited a profound reduction of viable cell number compared to DMSO control, the inventors observed a significantly enhanced antiproliferative effect for the drug combination vs. single drug treatment in three of the four cases (FIG. 7B). Morphologic changes within the combinatorial drug treatment group, seemed to be more profound than vehicle or either of the compounds alone.

Example 12

Combinatorial Menin—MLL and DOT1L Inhibition Synergistically Abolishes NPM1mut Leukemia Initiating Potential In Vivo Given the findings in previous examples, which showed synergistic drug effect for simultaneous menin-MLL and DOT1L inhibition in NPM1$^{mut}$ leukemias in vitro, the inventors tested the effects of combinatorial drug treatment on leukemia initiating potential. Equal numbers of viable Npm1$^{CA/+}$Rosa$^{SB/+}$ leukemia cells pretreated with drug vehicle, EPZ4777, MI-503, or the combination were transplanted into sublethally irradiated recipient mice and assessed for leukemia onset and survival. Whereas both, EPZ4777 and MI-503 treatment led to significantly prolonged survival compared to vehicle control, the inventors observed a significant survival advantage for the drug combination treatment compared to either of the compounds alone (FIG. 8A). Leukemia onset was also significantly delayed as reflected by significantly lower white cells count or CD45.2 engraftment at the time of death from leukemia within the control group (FIG. 8B). These data confirm that both menin-MLL and DOT1L inhibition diminishes leukemia initiation and indicate that simultaneous treatment using both compounds shows enhanced effects on leukemia initiating (stem) cells.

Methods

Cell Culture and Cell Lines

The AML cell lines OCI-AML3, OCI-AML2, SET-2, MOLM-13, HL-60, as well as 293T cells, and Hs27 cells were maintained under standard conditions. Cell line authentication testing (ATCC) verified identity and purity for all human AML cell lines used in this study. Murine leukemia cells were cultured in DMEM supplemented with 15% fetal bovine serum, 1% Penicillin/Streptomycin, and cytokines (SCF 100 ng/µl, IL-3 20 ng/µl, and IL-6 20 ng/µl).

CRISPR-Cas9 Screening

Plasmid construction and sgRNA design: The pCW-Cas9 expression construct (humanized *S. pyogenes* Cas9 containing N-terminal FLAG-tag and the TET ON promotor) and the pLKO5.sgRNA.EFS.GFP vector were both purchased from Addgene (#50661 and #57822). All sgRNAs in this study were designed using crispr.mit.edu/ and quality scores for all but 3 sgRNAs were above 70. Domain description, sgRNA sequences and quality scores from this study are provided in the tables below. sgRNA cloning was performed by annealing and ligating two oligonucleotides into a BsmB1-digested pLKO5.sgRNA.EFS.GFP vector as described{Heckl, 2014 #642}.

TABLE 3

MLL1 single guide RNAs (sgRNA)
(Table discloses SEQ ID NOS 1-25, respectively, in order of appearance)

| sgRNA Name | Target + PAM Sequence | Quality Score |
|---|---|---|
| N-HINGE-LOOP-1 | CGCCCCGCGGCAACGCGTCCCGG | 91 |
| N-HINGE-LOOP-2 | GGGCCGCCACCGCCGACCGGGGG | 87 |
| N-HINGE-LOOP-3 | CGAAGACGAGGCGGACGACGAGG | 78 |
| N-HINGE-LOOP-4 | TGACGAAGACGAAGACGAGGCGG | 54 |
| α1-MBM-LBM-1 | TGCAGCGCCGCGTCGAAGCCCGG | 93 |
| α1-MBM-LBM-2 | GCACCAACCTGCGCCGGTTCCGG | 93 |
| α1-MBM-LBM-3 | CTGCAGGTCTCGGCCGCCATCGG | 84 |
| α1-MBM-LBM-4 | GGTGGGCCCGGGCTTCGACGCGG | 84 |
| CXXC-1 | GACGTCGATCGAGGCGGTGTGGG | 99 |
| CXXC-2 | TATATTGCGACCACCAAACTTGG | 82 |
| CXXC-3 | TGCTTAGATAAGCCCAAGTTTGG | 72 |
| CXXC-4 | GTACAAACACCACAGTCCTCAGG | 70 |
| PHD-N-1 | AGAGGAGAACGAGCGCCCTCTGG | 84 |
| PHD-N-2 | TGCAAATTCTGTCACGTTTGTGG | 81 |
| PHD-N-3 | ACTCAGGGTGATAGCTGTTTCGG | 77 |
| PHDC-1 | TGTGAGACAGCAACCCACGGTGG | 82 |
| PHDC-2 | ACACATGAAGTGATAGTTGCTGG | 74 |
| BROM-1 | CCATTTGCTACGCTACCGGCAGG | 96 |
| BROM-2 | GTCTCGGGATTTAAGTCTGGAGG | 84 |
| BROM-3 | TGGTGGATCAGGTCCTTCGGGGG | 84 |
| BROM-4 | CAGCAGCCTTTAGATCTAGAAGG | 78 |
| SET-1 | GATGGAGCGGATGACGTTGCCGG | 89 |
| SET-2 | AAAAGACCCCGGCCATGGATGGG | 81 |
| SET-3 | GGAAAAGTATTACGACAGCAAGG | 80 |
| SET-4 | GAGATGGTGATTGAGTATGCCGG | 77 |

N-HINGE-LOOP = N-terminal hinge loop of the menin binding domain of MLL1 that spans a large distance on menin without many specific interactions. α1-MBM-LBM = N-terminal fragment of MLL1 containing the menin-binding and LEDGF-binding motif (as defined by Huange et al[1]), CXXC = CXXC domain; PHD-N = N-terminal PHD-finger domains; PHD-C = C-terminal PHD-finger domain; BROM = Bromodomain; SET = Set domain.

TABLE 4

MLL2 single guide RNAs
(Table discloses SEQ ID NOS 26-49, respectively, in order of appearance)

| sgRNA Name | Target + PAM Sequence | Quality Score |
|---|---|---|
| N-HINGE-LOOP-1 | CCCCGTTGCCCCGTCCGCCGCGG | 89 |
| N-HINGE-LOOP-2 | CAACGGGGCCGAAAGAGTGCGGG | 83 |
| α1-MBM-LBM-1 | ACGGCCCTGCTCCGTTTGCTGGG | 87 |
| α1-MBM-LBM-2 | CGTTTGCTGGGGCTCCGCCGGGG | 84 |
| α1-MBM-LBM-3 | GAGCCCCAGCAAACGGAGCAGGG | 76 |
| α1-MBM-LBM-4 | GGCCGTGTCCTCCCCGGGCTCGG | 60 |
| CXXC-1 | AAGATGCGCATGGCTCGATGTGG | 91 |
| CXXC-2 | TCGGGGCTGCCTACGTGTGCAGG | 90 |
| CXXC-4 | GGTGTTAGGGCCCCCAAACTTGG | 82 |
| PHD-N-1 | CAGCTCGTGGAGTCCTTTGCTGG | 78 |
| PHD-N-2 | AGCACCAGGTGTCGTGATGCTGG | 90 |
| PHD-N-3 | CCACGCGCAAACGGCGCCACTGG | 97 |
| PHD-N-4 | TGCATACCACCCGGCCTGTCTGG | 89 |
| PHDC-1 | AGTGCGCACAGTGCGATCACTGG | 94 |
| PHDC-2 | TCATAGCAGCGTGTACAGATCGG | 87 |
| PHDC-3 | CTGGTCGGCGGAAGTCTTCGAGG | 90 |
| PHDC-4 | CTGAAGCCTGGCGCCACGGTGGG | 84 |
| BROM-1 | AGCTGTGAGTCAGCGCTTCGAGG | 90 |
| BROM-2 | ACTCACAGCTTGCAGGCCGCAGG | 76 |
| BROM-3 | GATGGGAAGCAACTGCACCCAGG | 71 |
| BROM-4 | CAGCAGTGGGCCCACCACCTTGG | 62 |
| SET-1 | TAAGCGCAACATCGACGCGGGGG | 98 |
| SET-2 | CGGGTGCTATATGTTCCGCATGG | 93 |
| SET-3 | GGCGGCATTGCCATGCATCGTGG | 93 |

N-HINGE-LOOP = N-terminal hinge loop of the menin binding domain of MLL1 that spans a large distance on menin without many specific interactions. α1-MBM-LBM = N-terminal fragment of MLL1 containing the menin-binding and LEDGF-binding motif (as defined by Huange et al[1]), CXXC = CXXC domain; PHD-N = N-terminal PHD-finger domains; PHD-C = C-terminal PHD-finger domain; BROM = Bromodomain; SET = Set domain.

Engineering OCI-AML3pCW-Cas9: OCI-AML3-pCW-Cas9 cells were derived by retroviral transduction of the NPM1mut acute myeloid leukemia cell line (OCI-AML3) with pCW-Cas9, followed by puromycin selection. Cells were plated in methylcellulose to obtain single cell-derived clones, re-expanded in liquid culture, and aliquots frozen in liquid nitrogen. pCW-Cas9 was induced in each clone with doxycycline and screened by anti-flag western blot analysis for Cas9 expression. Three independent Cas9 expressing clones were infected with positive control sgRNAs targeting RPA3 and empty control vector to assess CRISPR-Cas9 editing efficiency after Cas9 induction. The two best performing clones were selected for the MLL and MLL2 domain screen: sgRNA virus production and negative selection screening. sgRNA virus production was performed in 96-well plates using HEK293T cells using the protocol provided at the Broad's Institute genetic perturbation platform (www.broadinstitute.org/rnai/public/resources/protocols) using the envelope and packaging plasmids pCMV-dR8.74psPAX2 and pMD2.G and X-tremeGENE transfection reagent (Roche). For virus transduction, OCI-AML3-pCW-Cas9 clones were thawed, plated in 96-well plates, and infected using virus supernatant. Three days following infection, GFP+/GFP− ratio was determined and doxycycline was added to the media to induce pCW-Cas9. GFP+/GFP− ratio was tracked every three days for 18 days as described {Shi, 2015 #598}.

Cell Viability Assays

Proliferation assays were performed as previously described. Viable cell counts were determined by flow cytometry using Sytox Blue (Invitrogen) or DAPI viability stains. For determination of $IC_{50}$ values EPZ004777, MI-2-2, and MI-503 were diluted 2-fold for a total of 9 concentration and vehicle control with the highest concentrations being 10 µM, 12 µM, and 10 µM respectively. Combinatorial drug treatment of serial dilutions of MI-2-2 or MI-503 with EPZ4777 was performed using constant ratios of 1.2:1 and 1:4 for assessment of drug synergism. Mathematical synergy testing was performed using CompuSyn software for Chou-Talalay-method based calculations (Chou T C, *Pharmacol Rev.* 2006 September; 58(3):621-81).

RNA Sequencing

Library construction and RNA sequencing was performed as described elsewhere (cite), comparing OCI-AML3 and OCI-AML2 cells treated for 7 days with 10 µM EPZ004777 or vehicle control in biological triplicates. For gene expression analysis 50 basepair single read sequencing was performed using a sequencing depth of 80 Million reads. ERCC control sequences were spiked into lysis buffer during RNA extraction. For fusion gene detection we performed 100 basepair paired-end sequencing at a depth of 80 Million reads. Computational analysis was performed using the Defuse algorithm.

Chromatin Immunoprecipitation

Chromatin immunprecipitation (ChIP) followed by qRT-PCR was performed as previously described (Bernt[23]). Briefly, cross-linking was performed with 1% formalin, and the cells were lysed in SDS buffer. Sonication was used to fragment DNA. ChIP for H3K79me2, Menin, and MLL was performed using the antibodies ab3534 (abcam), 300-150 (Bethyl), ab8580 (abcam) and Santa Cruz ac-899 (Rpb1 terminus) specific to the respective modifications. The antibodies are publicly available. Eluted DNA fragments were analyzed using qPCR. Primer sequences (all human) are as follows:

| Gene Name | FW Primer | RV Primer | primer per locus identifier |
|---|---|---|---|
| HOX49 | GGGAGACGGGAGAGTACAGA (SEQ ID NO: 50) | GCTCTACGATGGGGTTTGTT (SEQ ID NO: 58) | HOXA9F_Xi |

-continued

| Gene Name | FW Primer | RV Primer | primer per locus identifier |
|---|---|---|---|
| HOXA10 | CCCGAGCTGATGAGCGAGTC (SEQ ID NO: 51) | GCCAAATTATCCCACAACAATGTC (SEQ ID NO: 59) | HOXA10_Xi |
| HOXB2 | AGAGAGTCCCCATACGCTTG (SEQ ID NO: 52) | ATTTTGGGAGGGGGAGATTT (SEQ ID NO: 60) | HOXB2_2 |
| HOXB3 | gatcgtaaaaatcgccgaga (SEQ ID NO: 53) | tgtcaactccccaaaaccat (SEQ ID NO: 61) | HOXB3_1 |
| HOXB4 | ATCCAGCTGCAGAGAAAAGC (SEQ ID NO: 54) | GTTAGGTTACTGGCGGGTTG (SEQ ID NO: 62) | HOXB4_1 |
| HOXB8 | GGCTCCCTACCAGCAGAAC (SEQ ID NO: 55) | GAATAGGCTCTGGCGTTGC (SEQ ID NO: 63) | HOXB8_1 |
| MEIS1 | AGGTTTTGGGAGAACGTGTG (SEQ ID NO: 56) | CCTTTAGCACTTCGCAGGAG (SEQ ID NO: 64) | MEIS1_Xi |
| ACTB | CGTAGCACAGCTTCTCCTTAATGTC (SEQ ID NO: 57) | AGCGCGGCTACAGCTTCA (SEQ ID NO: 65) | ACTB_Xi |

Small Molecule Inhibitors

EPZ004777 was synthesized by James Bradner's laboratory (Dana Farber Cancer Institute, Boston, Mass.) but it is also available commercially, for example from MedChem Express (www.medchemexpress.com). EPZ-5676 and MI-2-2 were purchased from Chempartner. MI-503 was synthesized by Vitae Pharmaceutical Inc. For in vitro studies 10 mM stock solutions were prepared in DMSO and stored at −20° C. Serial dilutions of stock solutions were carried out just prior to use in each experiment, and final DMSO concentrations were kept at or below 0.01% and 0.02% for combination treatment experiments, respectively.

In Vitro Studies

RNA and DNA purification, cDNA synthesis, quantitative real-time (qRT-) PCR, western blotting, flow cytometry, colony forming assays, viral transduction and shRNA based knock down experiments were performed using standard procedures. Primer sequences, western antibodies, and plasmids are also listed in the supplement.

Mice, Murine Bone Marrow Transplantation Assays $Npm1^{CA/+}Flt3^{ITD/+}$ and $Npm1^{CA/+}Rosa^{SB/+}$ cells were harvested from moribund leukemic animals and transplanted into primary and $^{secondary}$ recipient mice as previously described. $Npm1^{CA/+}Flt3^{ITD/+}$ cells were transplanted into 6-8 week-old BL6/129 (Jackson Laboratory) or NSG mice (Taconic) and $Npm1^{CA/+}Rosa^{SB/+}$ into NSG mice (Taconic). Animals were preconditioned with 600 cGy or 200 cGy total body irradiation, respectively ($^{135}Cs$ source) and 12-24 hours following irradiation 1×10$^6$ leukemia cells were administered via tail vein injection. All transplantation experiments with ex vivo treated cells were performed as secondary transplantations.

OCI-AML3 Xenograft Model 7-10 week female NSG mice (Taconic) were injected via tail vein with 5×10$^6$ OCI-AML3 cells. Treatment was initiated 5 days post transplantation consisting of either vehicle (25% DMSO, 25% PEG400, 50% PBS) or MI-503 at 50 mg/kg IP, bid. N=2 mice and n=3 mice of each group were sacrificed after 7 and 12 days of drug treatment and leukemia burden was assessed by determining human CD45 using flow-cytometry from peripheral blood and bone marrow. For gene expression analysis, RNA was isolated from MACS sorted hCD45 cells and further processed using standard procedures. Remaining animals were treated for 15 consecutive days and then monitored daily for clinical symptoms to assess survival. Moribund animals were euthanized when they displayed signs of terminal leukemic disease.

Human AML Co-Culture Assay

Human AML samples were co-cultured with irradiated Hs27 stromal cells for 10 days in serum-free media (StemSpan, Stem Cell Technologies) supplemented with human cytokines, SR-1, and drug(s) or vehicle (DMSO, EPZ004777 10 μM, MI-503 2.5 μM, or EPZ004777 plus MI-503) as previously described. Experiments were performed in triplicates and DMSO concentrations were kept below 0.02%. Cell numbers were determined by flow cytometry using viability and anti-hCD45 staining to control for possible stromal cell contamination after 10 days. Cell differentiation was assessed using anti-hCD11b staining.

Data Analysis and Statistical Methods

Statistical significance was calculated using unpaired two-tailed Student's t test, survival was estimated using the Kaplan-Meier method. Computations were all performed using GraphPad Prism, version 6. Error bars represent mean+/−standard error of the mean.

REFERENCES

1. Sauvageau G, Landsdorp P M, Eaves C J, Hogge D E, Dragowska W H, Reid D S, et al. Differential expression of homeobox genes in functionally distinct CD34+ subpopulations of human bone marrow cells. Proc Natl Acad Sci USA. 1994 Dec. 6; 91(25):12223-7.
2. Giampaolo A, Sterpetti P, Bulgarini D, Samoggia P, Pelosi E, Valtieri M, et al. Key functional role and lineage-specific expression of selected HOXB genes in purified hematopoietic progenitor differentiation. Blood. 1994 Dec. 1; 84(11):3637-47.
3. Alharbi R A, Pettengell R, Pandha H S, Morgan R. The role of HOX genes in normal hematopoiesis and acute leukemia. Leukemia. 2013 April; 27(5):1000-8.
4. Spencer D H, Young M A, Lamprecht T L, Helton N M, Fulton R, O'Laughlin M, et al. Epigenomic analysis of the HOX gene loci reveals mechanisms that may control canonical expression patterns in AML and normal hematopoietic cells. Leukemia. 2015 June; 29(6):1279-89.

5. Argiropoulos B, Humphries R K. HOX genes in hematopoiesis and leukemogenesis. Oncogene. 2007 Oct. 15; 26(47):6766-76.
6. Mullighan C G, Kennedy A, Zhou X, Radtke I, Phillips L A, Shurtleff S A, et al. Pediatric acute myeloid leukemia with NPM1 mutations is characterized by a gene expression profile with dysregulated HOXgene expression distinct from MLL-rearranged leukemias. Leukemia. 2007 September; 21(9):2000-9.
7. Alcalay M, Tiacci E, Bergomas R, Bigerna B, Venturini E, Minardi S P, et al. Acute myeloid leukemia bearing cytoplasmic nucleophosmin (NPMc+ AML) shows a distinct gene expression profile characterized by up-regulation of genes involved in stem-cell maintenance. Blood. 2005 Aug. 1; 106(3):899-902.
8. Falini B, Mecucci C, Tiacci E, Alcalay M, Rosati R, Pasqualucci L, et al. Cytoplasmic nucleophosmin in acute myelogenous leukemia with a normal karyotype. N Engl J Med. 2005 Jan. 20; 352(3):254-66.
9. Schlenk R F, Dohner K, Krauter J, Frohling S, Corbacioglu A, Bullinger L, et al. Mutations and treatment outcome in cytogenetically normal acute myeloid leukemia. N Engl J Med. 2008 May 1; 358(18):1909-18.
10. Cancer Genome Atlas Research N. Genomic and epigenomic landscapes of adult de novo acute myeloid leukemia. N Engl J Med. 2013 May 30; 368(22):2059-74.
11. Verhaak R G, Goudswaard C S, van Putten W, Bijl M A, Sanders M A, Hugens W, et al. Mutations in nucleophosmin (NPM1) in acute myeloid leukemia (AML): association with other gene abnormalities and previously established gene expression signatures and their favorable prognostic significance. Blood. 2005 Dec. 1; 106(12):3747-54.
12. Schnittger S, Schoch C, Kern W, Mecucci C, Tschulik C, Martelli M F, et al. Nucleophosmin gene mutations are predictors of favorable prognosis in acute myelogenous leukemia with a normal karyotype. Blood. 2005 Dec. 1; 106(12):3733-9.
13. Buchner T, Berdel W E, Haferlach C, Haferlach T, Schnittger S, Muller-Tidow C, et al. Age-related risk profile and chemotherapy dose response in acute myeloid leukemia: a study by the German Acute Myeloid Leukemia Cooperative Group. J Clin Oncol. 2009 Jan. 1; 27(1):61-9.
14. Ostronoff F, Othus M, Lazenby M, Estey E, Appelbaum F R, Evans A, et al. Prognostic significance of NPM1 mutations in the absence of FLT3-internal tandem duplication in older patients with acute myeloid leukemia: a SWOG and U K National Cancer Research Institute/Medical Research Council report. J Clin Oncol. 2015 Apr. 1; 33(10):1157-64.
15. Federici L, Falini B. Nucleophosmin mutations in acute myeloid leukemia: a tale of protein unfolding and mislocalization. Protein science: a publication of the Protein Society. 2013 May; 22(5):545-56.
16. Okuwaki M, Matsumoto K, Tsujimoto M, Nagata K. Function of nucleophosmin/B23, a nucleolar acidic protein, as a histone chaperone. FEBS letters. 2001 Oct. 12; 506(3):272-6.
17. Krivtsov A V, Armstrong S A. MLL translocations, histone modifications and leukaemia stem-cell development. Nat Rev Cancer. 2007 November; 7(11):823-33.
18. Krivtsov A V, Twomey D, Feng Z, Stubbs M C, Wang Y, Faber J, et al. Transformation from committed progenitor to leukaemia stem cell initiated by MLL-AF9. Nature. 2006 Aug. 17; 442(7104):818-22.
19. Yokoyama A, Cleary M L. Menin critically links MLL proteins with LEDGF on cancer-associated target genes. Cancer Cell. 2008 Jul. 8; 14(1):36-46.
20. Yokoyama A, Somervaille T C, Smith K S, Rozenblatt-Rosen O, Meyerson M, Cleary M L. The menin tumor suppressor protein is an essential oncogenic cofactor for MLL-associated leukemogenesis. Cell. 2005 Oct. 21; 123(2):207-18.
21. Shi A, Murai M J, He S, Lund G, Hartley T, Purohit T, et al. Structural insights into inhibition of the bivalent menin-MLL interaction by small molecules in leukemia. Blood. 2012 Nov. 29; 120(23):4461-9.
22. Borkin D, He S, Miao H, Kempinska K, Pollock J, Chase J, et al. Pharmacologic inhibition of the Menin-MLL interaction blocks progression of MLL leukemia in vivo. Cancer Cell. 2015 Apr. 13; 27(4):589-602.
23. Bernt K M, Zhu N, Sinha A U, Vempati S, Faber J, Krivtsov A V, et al. MLL-rearranged leukemia is dependent on aberrant H3K79 methylation by DOT1L. Cancer Cell. 2011 Jul. 12; 20(1):66-78.
24. Deshpande A J, Deshpande A, Sinha A U, Chen L, Chang J, Cihan A, et al. AF10 regulates progressive H3K79 methylation and HOXgene expression in diverse AML subtypes. Cancer Cell. 2014 Dec. 8; 26(6):896-908.
25. Chen C W, Koche R P, Sinha A U, Deshpande A J, Zhu N, Eng R, et al. DOT1L inhibits SIRT1-mediated epigenetic silencing to maintain leukemic gene expression in MLL-rearranged leukemia. Nat Med. 2015 April; 21(4):335-43.
26. Deshpande A J, Bradner J, Armstrong S A. Chromatin modifications as therapeutic targets in MLL-rearranged leukemia. Trends in immunology. 2012 November; 33(11):563-70.
27. Daigle S R, Olhava E J, Therkelsen C A, Basavapathruni A, Jin L, Boriack-Sjodin P A, et al. Potent inhibition of DOT1L as treatment of MLL-fusion leukemia. Blood. 2013 Aug. 8; 122(6):1017-25.
28. Daigle S R, Olhava E J, Therkelsen C A, Majer C R, Sneeringer C J, Song J, et al. Selective killing of mixed lineage leukemia cells by a potent small-molecule DOT1L inhibitor. Cancer Cell. 2011 Jul. 12; 20(1):53-65.
29. Chen Y X, Yan J, Keeshan K, Tubbs A T, Wang H, Silva A, et al. The tumor suppressor menin regulates hematopoiesis and myeloid transformation by influencing HOX gene expression. Proc Natl Acad Sci USA. 2006 Jan. 24; 103(4):1018-23.
30. Maillard I, Hess J L. The role of menin in hematopoiesis. Advances in experimental medicine and biology. 2009; 668:51-7.
31. Shi J, Wang E, Milazzo J P, Wang Z, Kinney J B, Vakoc C R. Discovery of cancer drug targets by CRISPR-Cas9 screening of protein domains. Nature biotechnology. 2015 June; 33(6):661-7.
32. Vassiliou G S, Cooper J L, Rad R, Li J, Rice S, Uren A, et al. Mutant nucleophosmin and cooperating pathways drive leukemia initiation and progression in mice. Nat Genet. 2011 May; 43(5):470-5.
33. Mupo A, Celani L, Dovey O, Cooper J L, Grove C, Rad R, et al. A powerful molecular synergy between mutant Nucleophosmin and Flt3-ITD drives acute myeloid leukemia in mice. Leukemia. 2013 September; 27(9):1917-20.
34. Grembecka J, He S, Shi A, Purohit T, Muntean A G, Sorenson R J, et al. Menin-MLL inhibitors reverse oncogenic activity of MLL fusion proteins in leukemia. Nature chemical biology. 2012 March; 8(3):277-84.

35. Loven J, Orlando D A, Sigova A A, Lin C Y, Rahl P B, Burge C B, et al. Revisiting global gene expression analysis. Cell. 2012 Oct. 26; 151(3):476-82.
36. Gaidzik V I, Schlenk R F, Paschka P, Stolzle A, Spath D, Kuendgen A, et al. Clinical impact of DNMT3A mutations in younger adult patients with acute myeloid leukemia: results of the AML Study Group (AMLSG). Blood. 2013 Jun. 6; 121(23):4769-77.
37. Patel J P, Gonen M, Figueroa M E, Fernandez H, Sun Z, Racevskis J, et al. Prognostic relevance of integrated genetic profiling in acute myeloid leukemia. N Engl J Med. 2012 Mar. 22; 366(12):1079-89.
38. Andersson A K, Miller D W, Lynch J A, Lemoff A S, Cai Z, Pounds S B, et al. IDH1 and IDH2 mutations in pediatric acute leukemia. Leukemia. 2011 October; 25(10):1570-7.
39. Falini B, Gionfriddo I, Cecchetti F, Ballanti S, Pettirossi V, Martelli M P. Acute myeloid leukemia with mutated nucleophosmin (NPM1): any hope for a targeted therapy? Blood reviews. 2011 November; 25(6):247-54.
40. Martelli M P, Gionfriddo I, Mezzasoma F, Milano F, Pierangeli S, Mulas F, et al. Arsenic trioxide and all-trans retinoic acid target NPM1 mutant oncoprotein levels and induce apoptosis in NPM1-mutated AML cells. Blood. 2015 May 28; 125(22):3455-65.
41. Burnett A K, Hills R K, Green C, Jenkinson S, Koo K, Patel Y, et al. The impact on outcome of the addition of all-trans retinoic acid to intensive chemotherapy in younger patients with nonacute promyelocytic acute myeloid leukemia: overall results and results in genotypic subgroups defined by mutations in NPM1, FLT3, and CEBPA. Blood. 2010 Feb. 4; 115(5):948-56.
42. Hess J L, Yu B D, Li B, Hanson R, Korsmeyer S J. Defects in yolk sac hematopoiesis in Mll-null embryos. Blood. 1997 Sep. 1; 90(5):1799-806.
43. Yagi H, Deguchi K, Aono A, Tani Y, Kishimoto T, Komori T. Growth disturbance in fetal liver hematopoiesis of Mll-mutant mice. Blood. 1998 Jul. 1; 92(1):108-17.
44. Ernst P, Fisher J K, Avery W, Wade S, Foy D, Korsmeyer S J. Definitive hematopoiesis requires the mixed-lineage leukemia gene. Dev Cell. 2004 March; 6(3):437-43.
45. Jude C D, Climer L, Xu D, Artinger E, Fisher J K, Ernst P. Unique and independent roles for MLL in adult hematopoietic stem cells and progenitors. Cell Stem Cell. 2007 Sep. 13; 1(3):324-37.
46. McMahon K A, Hiew S Y, Hadjur S, Veiga-Fernandes H, Menzel U, Price A J, et al. Mll has a critical role in fetal and adult hematopoietic stem cell self-renewal. Cell Stem Cell. 2007 Sep. 13; 1(3):338-45.
47. Artinger E L, Mishra B P, Zaffuto K M, Li B E, Chung E K, Moore A W, et al. An MLL-dependent network sustains hematopoiesis. Proc Natl Acad Sci USA. 2013 Jul. 16; 110(29):12000-5.
48. Lee J H, Tate C M, You J S, Skalnik D G. Identification and characterization of the human Set1B histone H3-Lys4 methyltransferase complex. J Biol Chem. 2007 May 4; 282(18):13419-28.
49. Mishra B P, Zaffuto K M, Artinger E L, Org T, Mikkola H K, Cheng C, et al. The histone methyltransferase activity of MLL1 is dispensable for hematopoiesis and leukemogenesis. Cell reports. 2014 May 22; 7(4):1239-47.
50. Kühn M W W, Hadler M J, Daigle S R, Koche R P, Krivtsov A V, Olhava E J, et al. MLL partial tandem duplication leukemia cells are sensitive to small molecule DOT1L inhibition. Haematologica. 2015 May; 100(5): e190-3.
51. Sportoletti P, Varasano E, Rossi R, Mupo A, Tiacci E, Vassiliou G, et al. Mouse models of NPM1-mutated acute myeloid leukemia: biological and clinical implications. Leukemia. 2015 February; 29(2):269-78.
52. Wang G G, Pasillas M P, Kamps M P. Meis1 programs transcription of FLT3 and cancer stem cell character, using a mechanism that requires interaction with Pbx and a novel function of the Meis1 C-terminus. Blood. 2005 Jul. 1; 106(1):254-64.
53. Dohner K, Paschka P. Intermediate-risk acute myeloid leukemia therapy: current and future. Hematology/the Education Program of the American Society of Hematology American Society of Hematology Education Program. 2014 Dec. 5; 2014(1):34-43.
54. Klaus C R, Iwanowicz D, Johnston D, Campbell Calif., Smith J J, Moyer M P, et al. DOT1L inhibitor EPZ-5676 displays synergistic antiproliferative activity in combination with standard of care drugs and hypomethylating agents in MLL-rearranged leukemia cells. The Journal of pharmacology and experimental therapeutics. 2014 September; 350(3):646-56.
55. Falini B, Brunetti L, Martelli M P. Dactinomycin in NPM1-Mutated Acute Myeloid Leukemia. N Engl J Med. 2015 Sep. 17; 373(12):1180-2.

All cited references, patent or literature, are incorporated by reference in their entirety. The examples disclosed herein are illustrative and not limiting in nature. Details disclosed with respect to the methods described herein included in one example or embodiment may be applied to other examples and embodiments. Any aspect of the present disclosure that has been described herein may be disclaimed, i.e., exclude from the claimed subject matter whether by proviso or otherwise.

The invention claimed is:

1. A method for inhibiting proliferation and/or inducing apoptosis in a leukemia cell, comprising contacting the leukemia cell with an inhibitor of interaction between MLL and menin, wherein the leukemia cell exhibits an NPM1 mutation, and does not exhibit a genetic mutation, alteration, and/or abnormality that is an MLL-translocation (MLL-t), an MLL-rearrangement (MLL-r), or an MLL-partial tandem duplication (MLL-PTD).

2. The method of claim 1, wherein the leukemia cell is selected from the group consisting of an acute lymphocytic leukemia (ALL) cell and an acute myeloid leukemia (AML) cell.

3. The method of claim 1, wherein the inhibitor has an IC50 of from about 100 nM to about 10 μM, or from about 250 nM to about 5 μM, or from about 500 nM to about 1 μM.

4. The method of claim 1, wherein the inhibitor is selected from the group consisting of MI-0202, MI-503, MI-463, MI-136, ML-225, a compound of the formula:

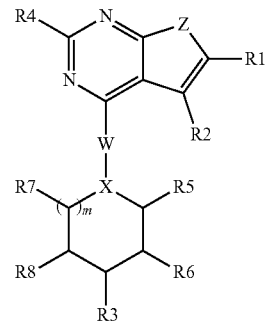

wherein R1, R2, R3, R4, R5, R6, R7, and R8 are each independently selected from the group consisting of: H, substituted or non-substituted alkyl, substituted or non-substituted alkoxy, a halogen (e.g. F, CI, Br, I, and At), a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; Z is S or O or NH or CH—CH; W is present or absent and is NH or NH—(CH$_2$)$_n$ (n is an integer between 0 and 10), or (CH$_2$)$_n$ (n is an integer between 0 and 10) or O or O—(CH$_2$)$_n$ (n is an integer between 0 and 10); X and Y are each independently N or C; and m is an integer between 0 and 3 or pharmaceutically acceptable salts of thereof: or a compound of the formula:

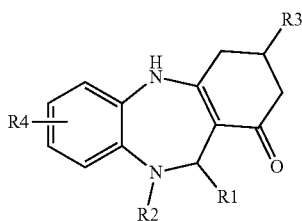

wherein R1, R2, R3, and R4 are each independently selected from the group consisting of: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused to the benzodiazepine ring system non-substituted or substituted with alkyl, aryl, halogen, hydrogen bond donor or acceptor, carbocyclic or heterocyclic aromatic ring comprising carbon; or pharmaceutically acceptable salts thereof.

5. A method for treating leukemia in a patient in need thereof, comprising:
   administering to the patient an effective amount of an inhibitor of interaction between MLL and menin;
   wherein the patient exhibits an NPM1 mutation, and does not exhibit a genetic mutation, alteration, and/or abnormality selected from the group consisting of an MLL-t, an MLL-r, and an MLL-PTD.

6. The method of claim 5, wherein the leukemia is selected from the group consisting of an acute lymphocytic leukemia (ALL) and an acute myeloid leukemia (AML).

7. The method of claim 5, wherein the inhibitor has an IC50 of from about 100 nM to about 10 µM, or from about 250 nM to about 5 µM, or from about 500 nM to about 1 µM.

8. The method of claim 5, wherein the inhibitor is selected from the group consisting of MI-0202, MI-503, MI-463, MI-136 and ML-225, and pharmaceutically acceptable salts or free base versions thereof or a compound of the formula:

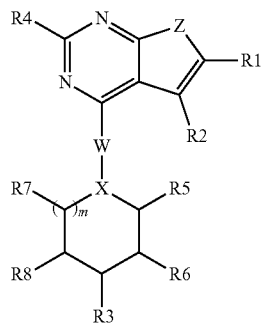

wherein R1, R2, R3, R4, R5, R6, R7, and R8 are each independently selected from the group consisting of: H, substituted or non-substituted alkyl, substituted or non-substituted alkoxy, a halogen (e.g. F, Cl, Br, I, and At), a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more of nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; Z is S or O or NH or CH—CH; W is present or absent and is NH or NH—(CH$_2$)$_n$ (n is an integer between 0 and 10), or (CH$_2$)$_n$ (n is an integer between 0 and 10) or O or O—(CH$_2$)$_n$ (n is an integer between 0 and 10); X and Y are each independently N or C; and m is an integer between 0 and 3; or pharmaceutically acceptable salts of thereof; or a compound of the formula:

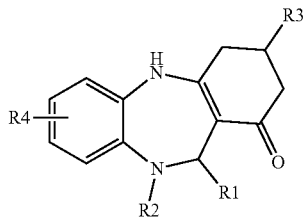

wherein R1, R2, R3, and R4 are each independently selected from the group consisting of: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused to the benzodiazepine ring system non-substituted or substituted with alkyl, aryl, halogen, hydrogen bond donor or acceptor, carbocyclic or heterocyclic aromatic ring comprising carbon; or pharmaceutically acceptable salts thereof.

9. A method according to claim 5 further comprising co-administering to the patient an effective amount of a DOT1L inhibitor.

10. The method of claim 9, wherein the DOT1L inhibitor inhibits DOT1L with an IC50 of from about 100 nM to about 10 µM, or from about 250 nM to about 5 µM, or from about 500 nM to about 1 µM.

11. The method of claim 9 wherein the DOT1L inhibitor is selected from the group consisting of a purine, a carbocycle-substituted purine, a 7-deazapurine, EPZ00477, EPZ005676, SGC-0946, SYC-522, SYC-534, and SYC-687.

12. The method of claim 1, wherein MLL is MLL1.

13. The method of claim 5, wherein MLL is MLL1.

* * * * *